US011254938B2

United States Patent
Brigstock et al.

(10) Patent No.: US 11,254,938 B2
(45) Date of Patent: Feb. 22, 2022

(54) COMPOSITIONS AND METHODS FOR TREATING HEPATIC FIBROSIS

(71) Applicant: Research Institute at Nationwide Children's Hospital, Columbus, OH (US)

(72) Inventors: David Brigstock, Dublin, OH (US); Li Chen, Dublin, OH (US)

(73) Assignee: Research Institute at Nationwide Children's Hospital, Columbus, OH (US)

(*) Notice: Subject to any disclaimer, the term of this patent is extended or adjusted under 35 U.S.C. 154(b) by 0 days.

(21) Appl. No.: 16/794,066

(22) Filed: Feb. 18, 2020

(65) Prior Publication Data

US 2020/0263178 A1 Aug. 20, 2020

Related U.S. Application Data

(63) Continuation of application No. 15/515,570, filed as application No. PCT/US2015/053019 on Sep. 29, 2015, now abandoned.

(60) Provisional application No. 62/057,971, filed on Sep. 30, 2014.

(51) Int. Cl.

| | | |
|---|---|---|
| *C12N 15/113* | (2010.01) | |
| *C12Q 1/6883* | (2018.01) | |
| *C12Q 1/68* | (2018.01) | |
| *C12N 15/11* | (2006.01) | |
| *A61K 31/00* | (2006.01) | |
| *A61K 9/19* | (2006.01) | |
| *A61K 31/7088* | (2006.01) | |
| *A61K 45/06* | (2006.01) | |

(52) U.S. Cl.
CPC .............. *C12N 15/113* (2013.01); *A61K 9/19* (2013.01); *A61K 31/00* (2013.01); *A61K 31/7088* (2013.01); *A61K 45/06* (2013.01); *C12N 15/11* (2013.01); *C12Q 1/68* (2013.01); *C12Q 1/6883* (2013.01); *C12N 2310/141* (2013.01); *C12N 2310/20* (2017.05); *C12N 2320/32* (2013.01); *C12N 2330/10* (2013.01); *C12Q 2600/106* (2013.01); *C12Q 2600/178* (2013.01); *G01N 2800/52* (2013.01); *G01N 2800/7052* (2013.01)

(58) Field of Classification Search
None
See application file for complete search history.

(56) References Cited

U.S. PATENT DOCUMENTS

| | | |
|---|---|---|
| 2009/0176723 A1 | 7/2009 | Brown et al. |
| 2010/0151480 A1 | 6/2010 | Taylor et al. |
| 2011/0003704 A1 | 1/2011 | Skog et al. |
| 2011/0124521 A1 | 5/2011 | Wang et al. |
| 2012/0045395 A1 | 2/2012 | Kaminski et al. |
| 2013/0078225 A1 | 3/2013 | Zeng et al. |
| 2013/0150426 A1 | 6/2013 | Kossen et al. |
| 2015/0053019 A1 | 2/2015 | Sulzer et al. |
| 2015/0301058 A1 | 10/2015 | Schettini et al. |
| 2016/0076098 A1* | 3/2016 | Ajit ........................ A61P 25/02 |
| | | 514/647 |
| 2016/0108368 A1 | 4/2016 | Larocca et al. |
| 2016/0298113 A1 | 10/2016 | Saetrom |
| 2018/0282810 A1 | 10/2018 | Brigstock et al. |

FOREIGN PATENT DOCUMENTS

| | | |
|---|---|---|
| WO | WO-2014/036429 A1 | 3/2014 |
| WO | WO-2016/054094 A1 | 4/2016 |
| WO | WO-2017/058938 A1 | 4/2017 |

OTHER PUBLICATIONS

Wu et al. Archives of Gynecology and Obstetrics pp. 1-11 (Year: 2021).*
Brigstock DR (2014) Riding the exosome shuttle in the liver. Cleveland Clinic, Cleveland OH May 20, 2014. Invited speaker.
Hunter, M.P. et al. (2008) "Detection of microRNA Expression in Human Peripheral Blood Microvesicles," PLoS One 3(11):e3694, 1-11.
Van Rooij, E. et al. (2008) "Dysregulation of microRNAs after myocardial infarction reveals a role of miR-29 in cardiac fibrosis," PNAS 105(35):13027-13032.
Vishnubhatla, I. et al. (2014) "The Development of Stem Cell-derived Exosomes as a Cell-free Regenerative Medicine," J Circ Biomark 3(31):1-14.
Xie, T. et al. (2011) "Comprehensive microRNA analysis in bleomycin-induced pulmonary fibrosis identifies multiple sites of molecular regulation," Physiol Genomics 43(9):479-487.
Xu, J. et al. (2011) "Circulating MicroRNAs, miR-21, miR-122, and miR-223, in Patients With Hepatocellular Carcinoma or Chronic Hepatitis," Molecular Carcinogenesis 50(2):136-142.
International Search Report and Written Opinion (ISA/US) in International Application No. PCT/US2015/053019, dated Dec. 29, 2015.
AASLD abstract from Li Chen and David Brigstock published in Hepatology 2014.
Bartel DP. MicroRNAs: genomics, biogenesis, mechanism, and function. Cell 2004; 116:281-97.
Brigstock DR (2013) Regulation of CCN2 fibrogenic pathways by exosomal microRNA. 7th Workshop of the International CCN Society, Nice France, Oct. 16-19, 2013.
Brigstock DR (2013) Regulation of liver fibrosis by microRNA. Chengdu Hospital, Chengdu, China Jul. 18 Invited Speaker.

(Continued)

*Primary Examiner* — Brian Whiteman
(74) *Attorney, Agent, or Firm* — Foley & Lardner LLP

(57) ABSTRACT

This disclosure provides pharmaceutical compositions and purified or isolated naturally occurring exosome products that have therapeutic use for treating an unmet medical need. The exosome compositions contain an effective amount of exosomes isolated from a body fluid of a non-diseased subject. The compositions are useful in the treatment of a variety of fibrotic diseases.

19 Claims, 14 Drawing Sheets

(56) References Cited

OTHER PUBLICATIONS

Brigstock DR (2014) Regulation of CCN2 fibrogenic pathways by exosomal microRNA. J Cell Comm Signal 8 p. 82.
Cervigne NK, Reis PP, Machado J, et al. Identification of a microRNA signature associated with progression of leukoplakia to oral carcinoma. Hum Mol Genet 2009; 18:4818-29.
Chang CJ, Hsu CC, Chang CH, et al. Let-7d functions as novel regulator of epithe lial-mesenchymal transition and chemoresistant property in oral cancer[J].Oncol Rep,2011,26(4):1003-1010 .doi:10.3892/or.2011.1360.
Charrier A, Chen L, Chen R, Hattori T, Takigawa M, Brigstock DR (2014) Production of nano-sized exosomes by fibrogenic cells of the liver or pancreas: Role in intercellular delivery of pro-fibrotic molecules and potential as novel drug delivery agents in vivo. 9th Annual Academic Surgical Congress, San Diego Feb. 4-6, 2014.
Charrier A, Chen L, Chen R, Hattori T, Takigawa M, Brigstock DR (2014) Production of nano-sized exosomes by fibrogenic cells of the liver or pancreas: Role in intercellular delivery of pro-fibrotic molecules and potential as novel drug delivery agents in vivo. J Surg Res 186 p. 678.
Chen L and Brigstock DR (2013) Exosomal microRNA modulates pathways of liver fibrosis by regulating connective tissue growth factor (CTGF) expression in fibrogenic cells during chronic injury. Experimental Biology Boston Apr. 20-24, 2013.
Chen L and Brigstock DR (2013) Exosomal microRNA modulates pathways of liver fibrosis by regulating connective tissue growth factor (CTGF) expression in fibrogenic cells during chronic injury. FASEB J. 27 Ib440.
Chen L and Brigstock DR (2013) Exosomal microRNA modulates pathways of liver fibrosis by regulating connective tissue growth factor (CTGF) expression in fibrogenic cells during chronic injury. International Society for Extracellular Vesicles, Boston Apr. 17-20, 2013.
Chen L, Brigstock DR (2012) Regulation of connective tissue growth factor (CTGF) expression in hepatic stellate cells by intercellular transfer of micro-RNA214: A paradigm for exosome-mediated control of fibrogenic signaling in the liver. Annual Meeting of AASLD, Boston, Nov. 9-13, 2012.
Chen L, Brigstock DR (2012) Regulation of connective tissue growth factor (CTGF) expression in hepatic stellate cells by intercellular transfer of micro-RNA214: A paradigm for exosome-mediated control of fibrogenic signaling in the liver. Hepatology 56 (suppl) A131.
Chen L, Charrier A, Brigstock D (2014) Connective tissue growth factor (CTGF/CCN2) expression in quiescent hepatic stellate cells is inhibited by a Twist-1-miR-214 axis. Club Hepatoma (Liver Pathobiology) Scientific Interest Group Poster Discussion and Networking Session. Sponsored by American Society for Investigative Pathology Group San Diego Apr. 29, 2014 (P47).
Chen L, Charrier A, Brigstock D (2014) Connective tissue growth factor (CTGF/CCN2) expression in quiescent hepatic stellate cells is inhibited by a Twist-1-miR-214 axis. Experimental Biology 2014 San Diego Apr. 25-29, 2014.
Chen L, Charrier A, Brigstock DR (2013) MicroRNA-214-mediated suppression of connective tissue growth factor (CTGF) in hepatic stellate cells is associated with stimulation of miR-214 promoter activity by cellular or exosomal Twist-1. Annual Meeting of AASLD Washington DC, Nov. 1-5, 2013.
Chen L, Charrier A, Brigstock DR (2013) MicroRNA-214-mediated suppression of connective tissue growth factor (CTGF) in hepatic stellate cells is associated with stimulation of miR-214 promoter activity by cellular or exosomal Twist-1. Hepatology 58 4 (Suppl) Abstract #28 p. 221A.
Chen L, Charrier A, Zhou Y, Brigstock DR (2012). The pro-fibrotic molecule, connective tissue growth factor (CTGF), is regulated by microRNA-214 (miR-214) in hepatic stellate cells. J. Surg. Res. 172 (2) A15.5.
Chen L, Charrier A, Zhou Y, Yu B, Agarwal K, Tsukamoto H, Lee LJ, Paulaitis ME, Brigstock DR (2014) Epigenetic regulation of connective tissue growth factor by delivery of microRNA-214 in exosomes from mouse or human hepatic stellate cells Hepatology 59 1118-1129 PMID: 24122827.
Chen L, Charrier, A, Zhou Y, Brigstock DR (2012) Up-regulation of connective tissue growth factor (CTGF) during liver fibrosis is associated with suppression of hepatic microRNA-214 (miR-214) expression: Identification of CTGF mRNA as a direct target of miR-214 in hepatic stellate cells. Annual Meeting of AASLD, Boston, Nov. 9-13, 2012 Awarded Presidential Poster of Distinction.
Chen L, Charrier, A, Zhou Y, Brigstock DR (2012) Up-regulation of connective tissue growth factor (CTGF) during liver fibrosis is associated with suppression of hepatic microRNA-214 (miR-214) expression: Identification of CTGF mRNA as a direct target of miR-214 in hepatic stellate cells. Hepatology 56 (suppl) A1194.
Chen L, Chen R, Brigstock DR (2014) Determination of signature microRNAs in experimental liver fibrosis by miRnome profiling of circulating exosomes Mol Biol Cell 25 (suppl) P1578).
Chen L, Chen R, Brigstock DR (2014) Determination of signature microRNAs in experimental liver fibrosis by miRnome profiling of circulating exosomes. Annual Meeting of ASCB, Philadelphia, Dec. 6-10.
Chen L, Chen R, Brigstock DR (2014) MicroRNA profiling of circulating exosomes during experimental liver fibrosis. Annual Meeting of AASLD Washington DC, Nov. 7-11, 2014.
Chen L, Chen R, Brigstock DR (2014) MicroRNA profiling of circulating exosomes during experimental liver fibrosis. Hepatology 60 1 (Suppl) Abstract #430 p. 412A.
Chen L, Chen R, Brigstock DR (2014) MicroRNA profiling of circulating exosomes during experimental liver fibrosis. NCH Research Institute Retreat, Columbus OH Sep. 17, 2014.
Chen L, Chen R, Kemper S, Brigstock DR (2015) Binding of hepatic stellate cell (HSC)-secreted exosomes to HSC is heparin- and integrin-dependent Annual Meeting of AASLD San Francisco Nov. 13-17, 2015 Awarded Presidential Poster of Distinction.
Chen L, Chen R, Kemper S, Brigstock DR (2015) Binding of hepatic stellate cell (HSC)-secreted exosomes to HSC is heparin- and integrin-dependent Hepatology 62 (Suppl) A1356 p. 875A.
Chen L, Chen R, Kemper S, Brigstock DR (2015) Circulating exosomes from healthy mice attenuate hepatic stellate cell activation and are anti-fibrotic in vivo Annual Meeting of AASLD San Francisco Nov. 13-17, 2015.
Chen L, Chen R, Kemper S, Brigstock DR (2015) Circulating exosomes from healthy mice attenuate hepatic stellate cell activation and are anti-fibrotic in vivo Hepatology 62 (Suppl) A192 p. 306A.
Chen L, Chen R, Kemper S, Charrier A, Brigstock DR (2015) Suppression of fibrogenic signaling in hepatic stellate cells by Twist1-dependent microRNA-214 expression: Role of exosomes in horizontal transfer of Twist1. American Journal of Physiology: Gastrointestinal and Liver Physiology 309 G491-499 PMID:26229009.
Chen L, Tsukamoto L, Brigstock D (2011) Ethanol-dependent expression of connective tissue growth factor is associated with down-regulation of microRNA 214 Gastroenterology 140 (Suppl 1) S-916.
Chen, L et al. "Epigenetic Regulation of Connective Tissue Growth Factor by MicroRNA-214 Delivery in Exosomes From Mouse or Human Hepatic Stellate Cells," Hepatology (2014) 59(3): 1118-29.
Chen, L., et al., "Regulation of connective tissue growth factor (CTGF) expression in hepatic stellate cells by intercellular transfer of micro-RNA214: A paradigm for exosome-mediated control of fibrogenic signaling in the liver", Oct. 2012 at the AASLD annual meeting, Hepatology 56 (suppl) A131).
Cong M, Chen L, Liu T, Wang P, Jia J, Brigstock D, You H (2015) MicroRNA profiling of circulating exosomes in HBV cirrhosis patients following anti-HBV therapy. Annual Meeting of AASLD San Francisco Nov. 13-17, 2015.
Cong M, Chen L, Liu T, Wang P, Jia J, Brigstock D, You H (2015) MicroRNA profiling of circulating exosomes in HBV cirrhosis patients following anti-HBV therapy. Hepatology 62 (Suppl) A1404 p. 896A.
Gorenchtein M, Poh CF, Saini R, et al. MicroRNAs in an oral cancer context-from basic biology to clinical utility. J Dent Res 2012;91:440-6.

(56) References Cited

OTHER PUBLICATIONS

International Preliminary Report on Patentability in International Application No. PCT/US2015/053019, dated Apr. 4, 2017.
Li J, Huang H, Sun L, et al. MIR-21 indicates poor prognosis intongue squamous cell carcinomas as an apoptosis inhibitor [J]. ClinCancer Res, 2009, 15(12): 3998-4008.doi: 10.1158/ 1078-0432. CCR-08-3053.
Liu X, Wang A, Heidbreder CE, et al. MicroRNA-24 targeting RNAbinding protein DND1 in tongue squamous cell carcinoma[J]. FEBS Lett,2010,584(18):4115-4120.doi:10.1016/j. Febslet.2010.08. 040.
Lu YC, Chang JT, Liao CT, et al. Oncomi R-196 promotes an invasive phenotype in oral cancer through the NME4-JNK-TIMP1-MMP signaling pathway [J]. Mol Cancer, 2014, 13:218. 10.1186/1476-4598-13-218.
Momen-Heravi F, Trachtenberg AJ, Kuo WP, et al. Genomewide study of salivary MicroRNAs for detection of oral cancer [J]. J Dent Res, 2014, 93 (7suppl): 86S-93S. doi: 10.1177/0022034514531018.
Tiwari A, Shivananda S, Gopinath KS, et al. MicroRNA-125a reduces proliferation and invasion of oral squamous cell carcinoma cells by targeting estrogen-related receptor alpha: Implications for Cancer Therapeutics [J].J Biol Chem, 2014, 289 (46): 32276-32290. doi: 10.1074/jbc.M114.584136. Epub Sep. 29, 2014. Withdrawal Notice [J Biol Chem. 2019].
Wu BH, Xiong XP, Jia J, et al. MicroRNAs: new actors in the oral cancer scene. Oral Oncol 2011; 47:314-9.
Zhu G, He Y, Yang S, et al. Identification of Gene and MicroRNA Signatures for Oral Cancer Developed from Oral Leukoplakia. Biomed Res Int 2015; 2015: 841956.
Non-Final Office Action on Appl. U.S. Appl. No. 15/515,570 dated Aug. 19, 2019 (25 pages).
Ha et al., "Exosomes as therapeutic drug carries and delivery vehicles across biological membranes: current perspectives and future challenges", Acta Pharm Sin B. 6:287-296 (Year: 2016).
U.S. Restriction Requirement for Appl. U.S. Appl. No. 15/515,570 dated Mar. 28, 2019 (10 pages).
Bostjancic et al., "Hepatic expression of miR-122, miR-126, miR-136 and miR-181a and their correlation to histopathological and clinical characteristics of patients with hepatitis C", Journal of Viral Hepatitis, 2014, 22(2): pp. 144-155. First published: Jul. 25, 2014.
Li et al., "Exosomes derived from human umbilical cord mesenchymal stem cells alleviate liver fibrosis", Stem Cells Dev. Mar. 15, 2013;22(6), pp. 845-854.
Li et al., "Overexpression of miR-483-5p/3p cooperate to inhibit mouse liver fibrosis by suppressing the TGF-beta stimulated HSCs in transgenic mice", J. Cell Mol. Med., 2014, vol. 18, No. 6, pp. 966-974.
WU et al., "Profiling Circulating MicroRNA Expression in Experimental Sepsis Using Cecal Ligation and Puncture", PLoS One, 2013, vol. 8, Issue 10: e77936, 11 pages.
Zhang et al., "Secreted monocytic miR-150 enhances targeted endothelial cell migration", Molecular Cell, 2010, 39(1), pp. 133-144.
De Minicis, S. et al. Cellular and Molecular mechanisms of hepatic fibrogenesis leading to liver cancer. Transl Gastrointest. Cancer 2012; 1:88-904.

\* cited by examiner

A
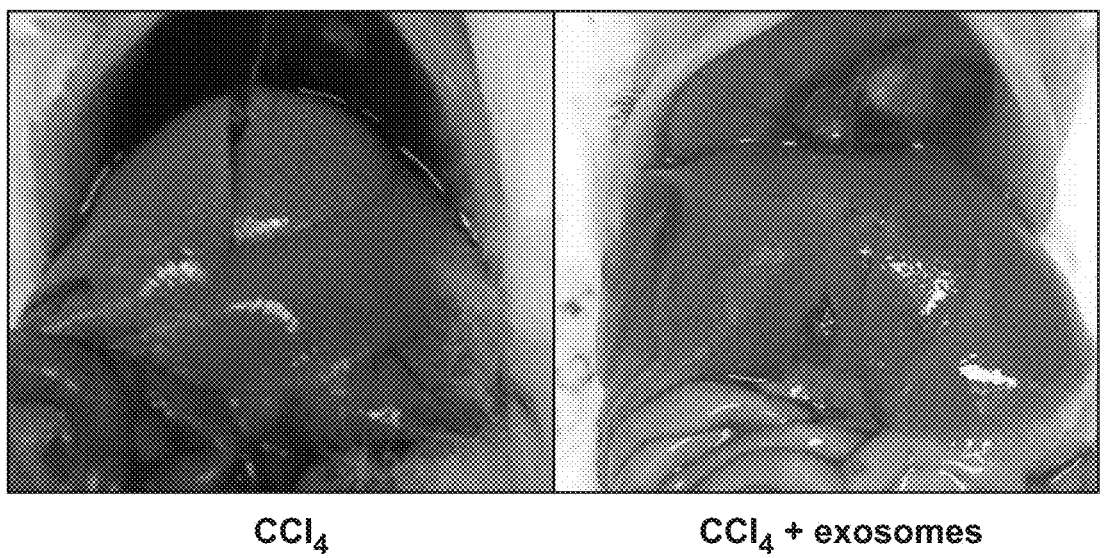
CCl₄            CCl₄ + exosomes
B
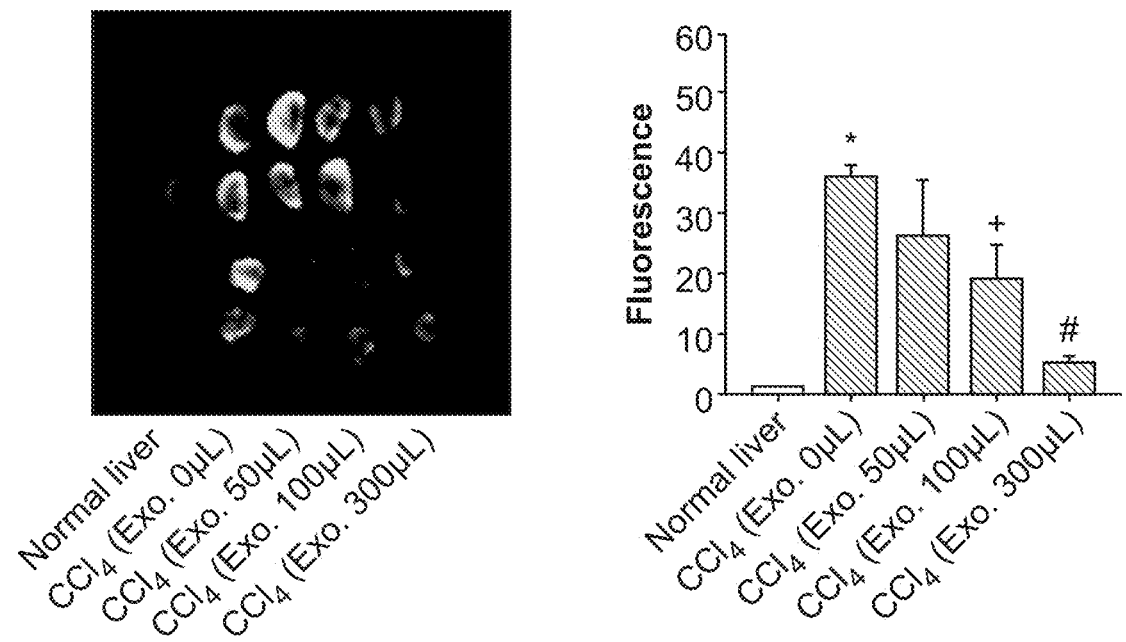
FIGS. 4A-4E

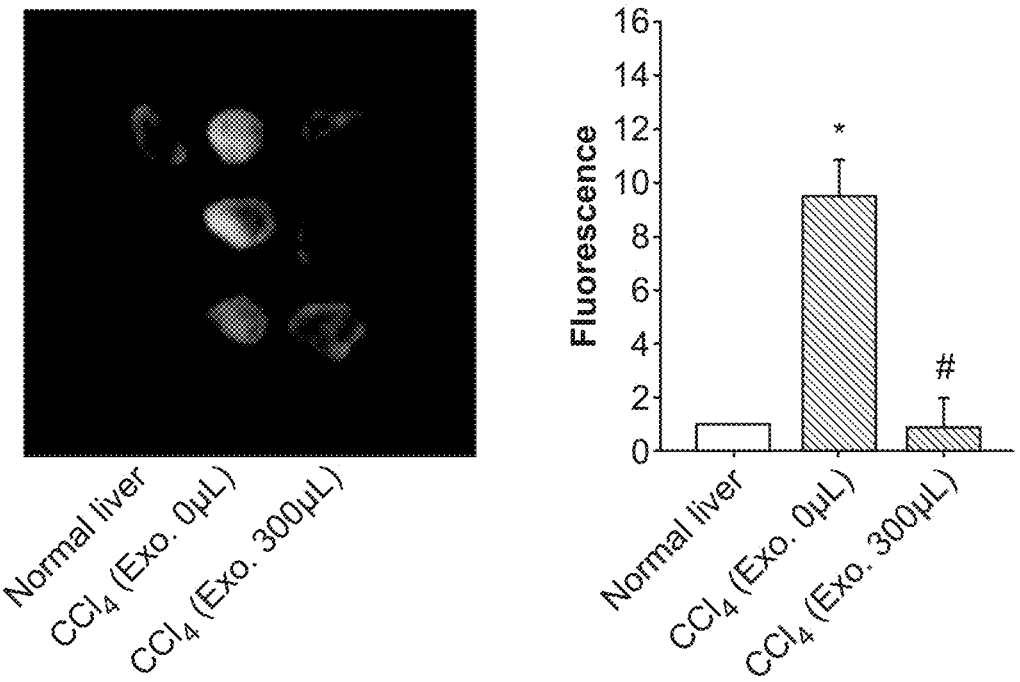
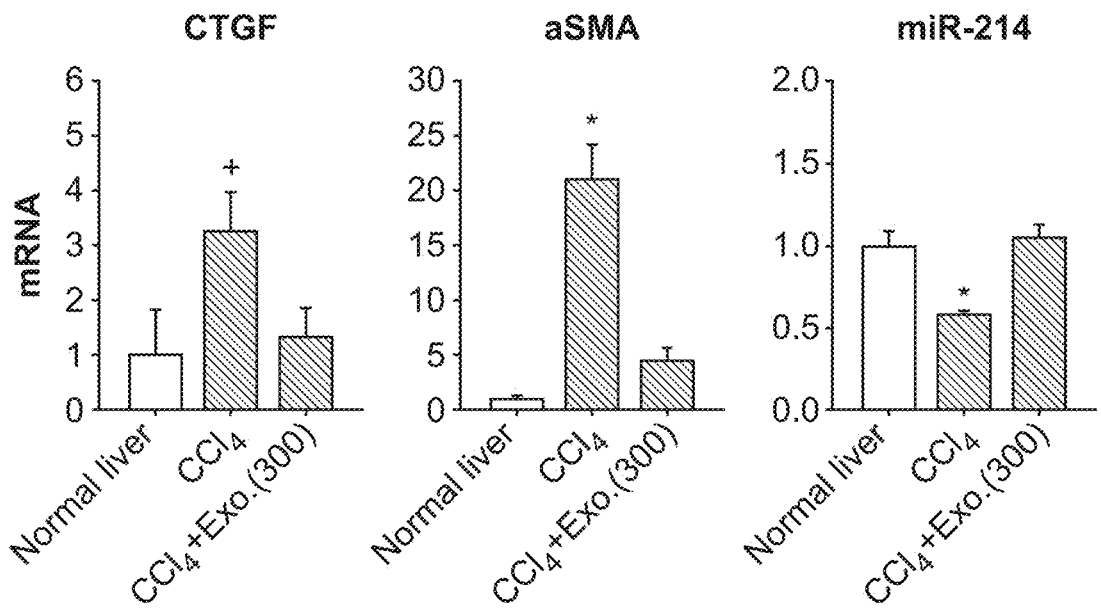
FIGS. 4A-4E (Cont. 1)

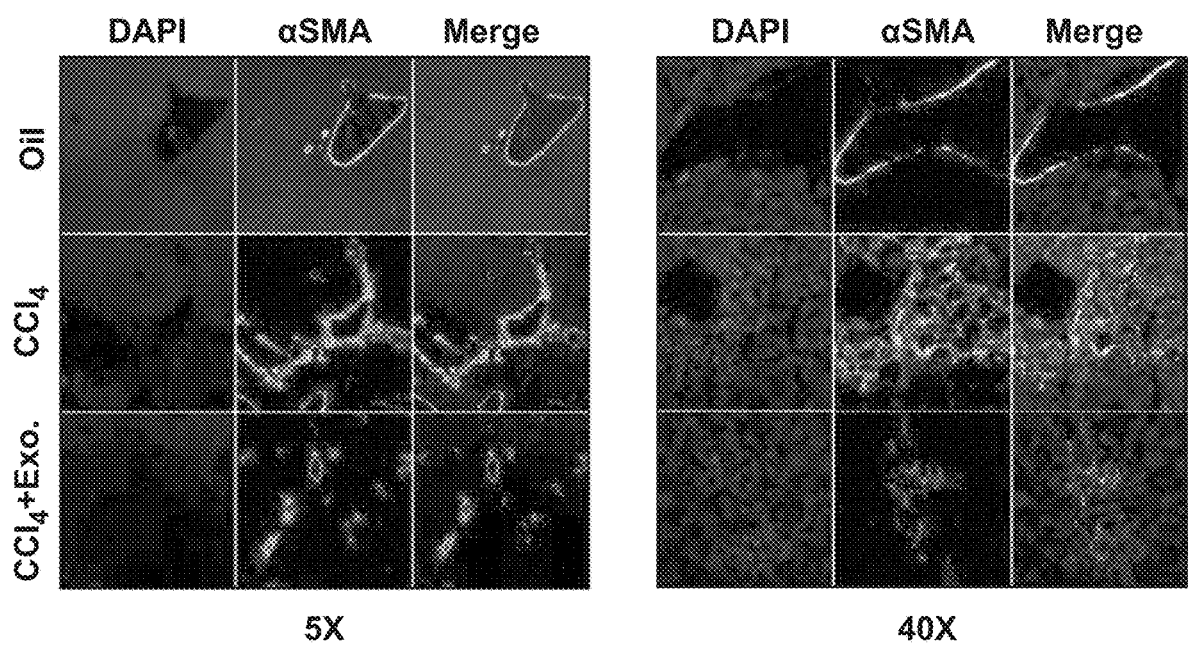
FIGS. 4A-4E (Cont. 2)

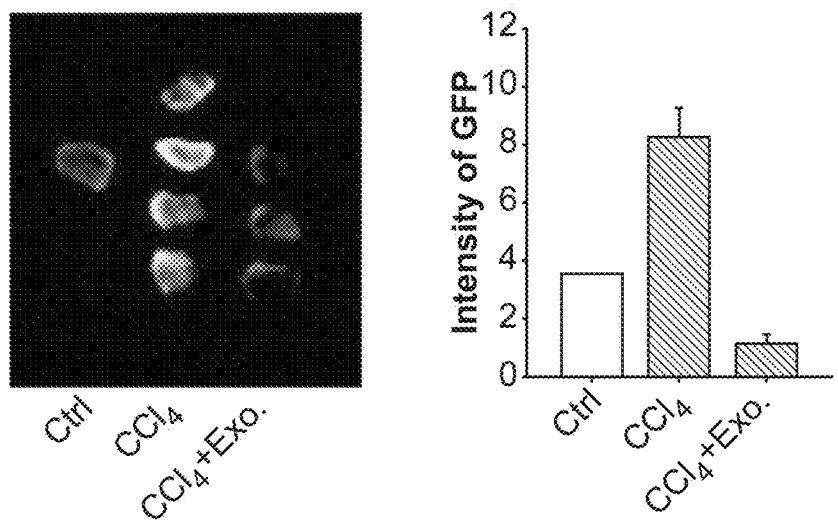
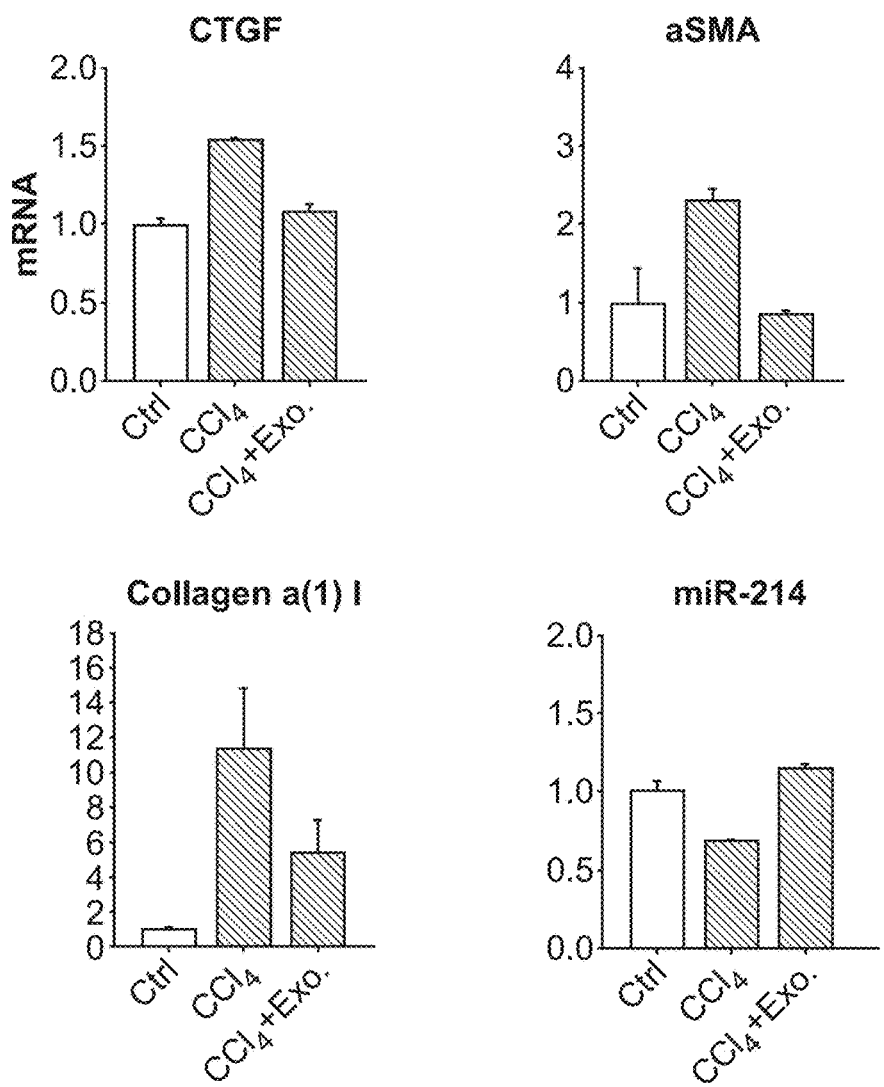
FIGS. 5A-5D

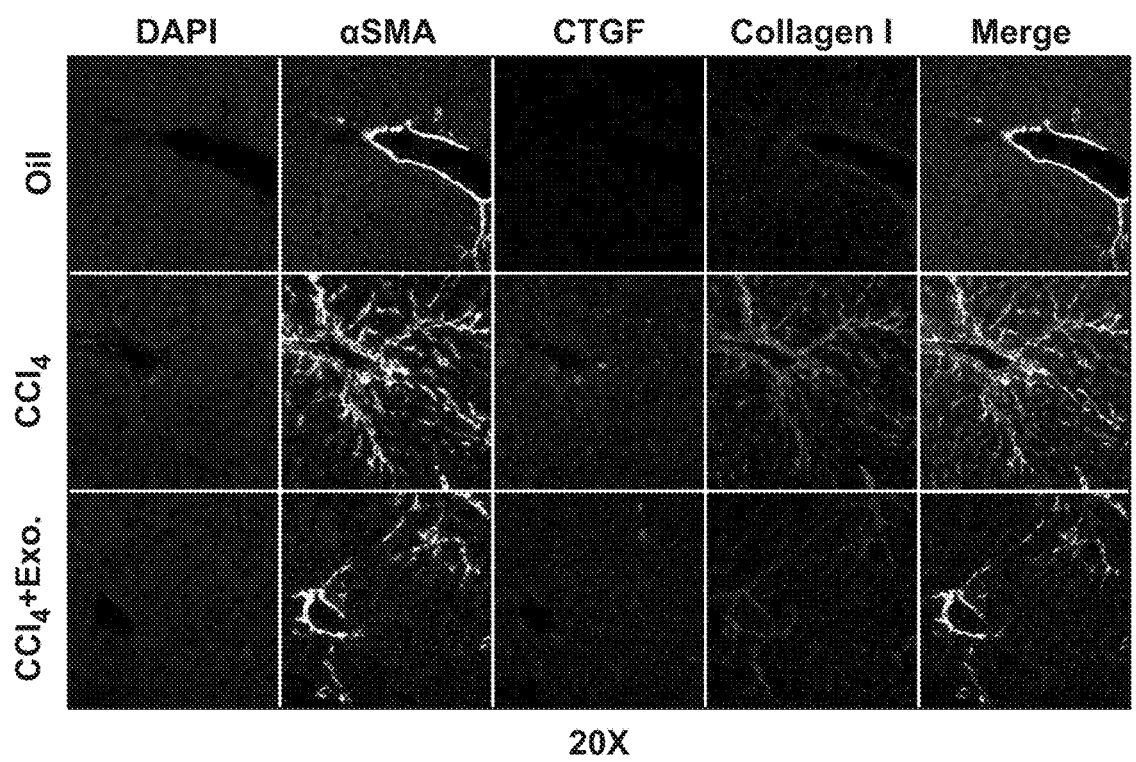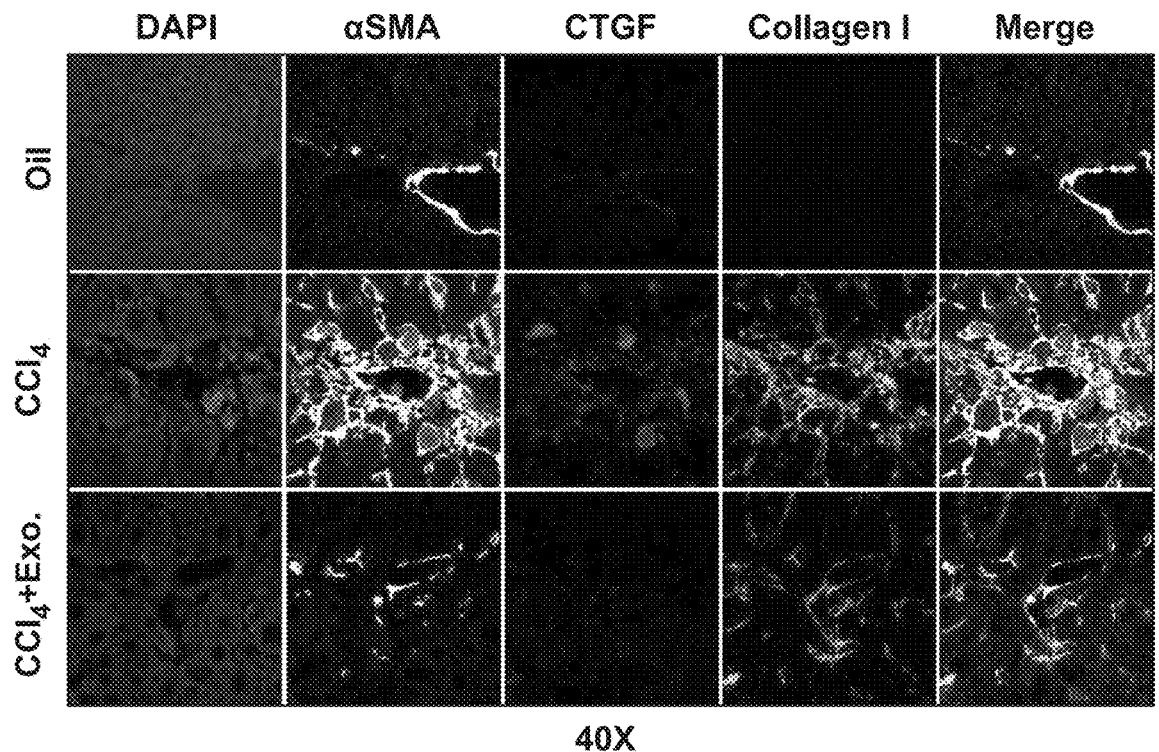
FIG. 5A-5D (Cont.)

| Healthy_HIGH | Healthy_LOW |
|---|---|
| 455-3p | 1906 |
| 23b-3p | 677-3p |
| 106a-3p | 541-3p |
| 200b-5p | 125b-1-3p |
| 532-5p | 500-5p |
| 34c-3p | 466j |
| 151-3p | 544-3p |
| 653-5p | 1a-2-5p |
| 687 | 1194 |
| 483-5p | 700-5p |

| ORGAN FIBROSIS | | | |
|---|---|---|---|
| Organ | Disorder | Cause | US Prevalance |
| Liver | Hepatic fibrosis/cirrhosis | Hepatitis A/B/C, alcoholic liver disease, non-alcoholic steatosis, biliary atresia, congenital | 400,000 |
| Heart | Cardiac fibrosis, cardiomyopathy | Aortic stenosis, emboli, hypertension | 100,000 |
| Kidney | End-stage renal disease | Diabetes, glomerulonephritis, hypertension | 250,000 |
| Lung | Pulmonary fibrosis, idiopathic pulmonary fibrosis | Environmental toxins, idiopathic | 150,000 |
| Pancreas | Chronic pancreatitis Pancreatic desmoplasia | Alcohol consumption, episodic recurrent acute pancreatitis Pancreatic adenocarcioma | 175,000 |
| Eye | Macular degeneration | Age-related, diabetes, hypertension | 400,000 |

FIG. 9

| POST - SURGICAL FIBROSIS |||
|---|---|---|
| Surgical Procedure | US procedures / yr | Fibrosis |
| Tendon/peripheral nerve | 1,000,000 | Scarring within tendon sheaths and at nerve endings |
| Discectomy | 420,000 | Epidural fibrosis |
| Laminectomy | 400,000 | Peridural fibrosis |
| Arthroplasty | 650,000 | Peripatellar fibrosis |
| Cataract | 500,000 | Capsular fibrosis in 50% of patients |
| Glaucoma | 150,000 | Fibrosis closes the created fistula; 30% failure rate |
| Abdominal surgery | 1,000,000 | Abdominal adhesions, significant morbidity |
| Ob/Gyn surgery | 1,700,000 | Infertility secondary to scarring |
| Angioplasty | 400,000 | Fibrotic artery blockage (restenosis) in 40% of cases |
| Coronary bypass | 400,000 | Mediastinal fibrosis, Intimal fibrosis Endoluminal fibrosis |
| Organ transplant | 60,000 | Transplant failure |
| Plastic/revision surgery | 170000 | Scarring unavoidable |
| Dermal surgery | 42 million | Scarring of skin in most cases |
| OTHER FORMS OF FIBROSIS |||
| Cause | US incidence | Cause |
| Scleroderma | 100,000 | Various, some unknown |
| Keloids | 300,000 | Skin trauma, genetic |
| Rheumatoid arthritis | 1.5 million | Fibrotic deposition in joint |
| Hypertrophic scars | 450,000 | Trauma / burns |
| Eye/corneal scars | 275,000 | Laser surgery, trauma, injury |

FIG. 9 (Cont.)

COMPOSITIONS AND METHODS FOR TREATING HEPATIC FIBROSIS

CROSS-REFERENCE TO RELATED APPLICATIONS

This application is a continuation application of U.S. application Ser. No. 15/515,570, filed Mar. 29, 2017, which is a national phase application under 35 U.S.C. § 371 of International Application No. PCT/US2015/053019, filed Sep. 29, 2015, which in turn claims priority under 35 U.S.C. § 119(e) to U.S. Provisional Application No. 62/057,971, filed Sep. 30, 2014, the content of each of which is hereby incorporated by reference in its entirety.

STATEMENT OF FEDERAL FUNDING

This invention was made with government support under Grant No. 1R01AA021276-01 awarded by National Institute on Alcohol Abuse and Alcoholism (NIAAA) of National Institutes of Health (NIH). The government has certain rights in the invention.

BACKGROUND

Chronic scarring, or "fibrosis", of the liver, lung, kidney, heart and other vital organ systems has no effective treatment, and is estimated to account for up to 45% of all deaths in the industrialized world. There are currently no FDA or EMEA-approved antifibrotic therapies.

Fibrosis is a common and debilitating pathology in many chronic liver diseases that hinders effective treatment and heightens the need for liver transplantation. Hepatic fibrosis is a common response to chronic injury and inflammation in the liver, resulting in excessive production and deposition of insoluble collagen and extracellular matrix components.

Affecting 5.5 million American adults (i.e. 2-3% of the adult US population), hepatic fibrosis is a serious medical problem because it compromises normal hepatic structure and function and is a harbinger of cirrhosis, hepatocarcinoma, and end-stage liver disease. Liver fibrosis is most commonly seen in patients with chronic liver injury (hepatitis and alcohol abuse) although the pediatric population can be affected as well (biliary atresia, congenital). With the current explosion of obesity-related health problems such as fatty livers, a huge increase in the number of patients at risk for or who have developed liver fibrosis is to be expected. There are many other types of scarring that lack effective treatment. For example, dermal scarring and abdominal adhesions occur in a high proportion of the >42 million surgeries performed each year in the United States but, again there is no FDA-approved medication to prevent or reduce scars. This market alone is estimated at $4 billion.

Thus, a need exists for effective and safe treatments for hepatic fibrosis. This disclosure satisfies these needs and provides related advantages as well.

SUMMARY

This disclosure provides pharmaceutical compositions and purified or isolated products that have therapeutic use for treating an unmet medical need. As disclosed in more detail herein, this disclosure provides a pharmaceutical comprising, or alternatively consisting essentially of, or yet further consisting of, a pharmaceutically acceptable carrier and an effective amount of miRNA and/or exosomes isolated from a body fluid of a non-diseased subject. In one aspect, the disease is a fibrotic disease or liver disease, e.g., liver fibrosis and the exosomes have a unique molecular profile in that the microRNA (miR or miRNA) and/or the miRNA profile of the exosomes comprise the lack of up-regulation of one or both of the markers miR-26b and/or -122, as compared to the exosome miR profile of a subject that is suffering from a liver or a fibrotic disease or an associated disorder. In one aspect the compositions comprise, or alternatively consist essentially of, or yet further consist of, one or more, two or more, three or more, four or more, five or more, six or more, seven or more, eight or more, nine or more, ten or more, eleven or more, twelve or more, thirteen or more, fourteen or more, fifteen or more, sixteen or more, or alternatively all of miR-9, -196b, miR-27a, -192, -214, -377, -455, -23b, -106a, -200b, -532, -34c, -151, -653, -687, and/or -483. These compositions are useful for the treatment of disease, such as fibrotic disease, hepatic liver disease and associated disorders.

This disclosure also provides a pharmaceutical compositions comprising, or alternatively consisting essentially of, or yet further consisting of, a pharmaceutically acceptable carrier and an effective amount of exosomes isolated from a body fluid of a non-diseased subject. In one aspect, the exosomes have a unique molecular profile in that the microRNA (miR) comprises the lack of down-regulation of one or both of the markers miR-9 and/or -196b, as compared to the exosome miR profile of a subject that is suffering from a liver or fibrotic disease or an associated disorder.

In further aspect, the exosomes of the above-noted compositions are identified by the microRNA (miR) profile by the lack of up-regulation of miR-26b and/or -122 and/or lack of down-regulation of miR-9 and/or -196b in the exosomes, as compared to the exosome miR profile of a subject that is suffering from a fibrotic disease, a liver disease, or an associated disorder.

In further aspect, the exosomes of the above-noted compositions are further identified by the microRNA (miR) exosome profile by the lack of up-regulation of one or more, two or more, three or more, four or more, and all of (and all integers there between) of miR-7a, -21, -22, -24, -26b, -34a, -155, -122, -1906, -195, 677, -541, -125b, -500, -466j, -544, -1a-2, -1194, and/or -700- and/or lack of down-regulation of one or more, two or more, three or more, four or more, and all of (and all integers there between) miR-27a, -192, -9, -196b, -214, -377, -455, -23b, -106a, -200b, -532, -34c, -151, -653, -687, and/or -483 in the exosomes, as compared to the exosome miR profile of a subject that is suffering from a liver or fibrotic disease or an associated disorder.

For each of the above compositions, the fluid from which the exosomes are isolated or purified is selected from the group of blood, serum, urine, lymphatic fluid, saliva, breast milk and/or plasma. The fluids can be maintained separately or combined from the same or multiple donors.

The compositions can then be administered to subjects identified as likely to have liver or hepatic disease or an associated disorder.

The compositions are useful for the preparation of a medicament and/or to perform methods for one or more of: a) inhibiting the progression of, b) preventing or c) treating, liver fibrosis or an associated disorder in a subject in need thereof. The methods comprise, or alternatively consist essentially of, or yet further consist of, administering to the subject an effective amount of the pharmaceutical composition described above. Non-limiting examples of an associated disorder is selected from the group of: inflammation of the liver, high deposition of lipids, high deposition of insoluble collagen, high deposition of extracellular matrix components, cirrhosis, hepatocarcinoma, and end-stage liver disease. These conditions are well known in the art and can be diagnosed by a treating physician.

The therapy and patient's health can be monitored by determining the level of one or more, two or more, three or more, or all of miR-26b, -122, miR-9 and/or -196b in a sample isolated from the patient prior to, during and after the therapy. In a further aspect, the therapy and patient's health and therapy response can be monitored by determining the level of one or more, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or twenty-eight or more, or twenty-nine or more, or thirty or more, or thirty-one or more, or thirty-two or more, or thirty-three or more, or thirty-four or more, or all of miR-21, -22, -7a, -24, -155, -195, -34a, -26b, -122, -9, -196b, -677, -541, -125b, -500, -466j, -544, -1a-2, -1194, -700, -27a, -192, -214, -377, -1906, -455, -23b, -106a, -200b, -532, -34c, -151, -653, -687, and/or -483, in a sample isolated from the patient prior to, during and after the therapy and wherein high levels of one or more of miR-21, -22, -7a, -24, -155, -195, -34a, -1906, 26b, -122, -677, -541, -125b, -500, -466, -544, -1a-2, -1194 and/or -700, and one or more of low levels of miR-9, -377, -27a, -192, -214, -196b, -455, -23b, -106a, -200b, -532, -34c, -151, -653, -687, and/or -483, identifies the patient as likely to have hepatic disease.

In one aspect, this disclosure also provides determining the hepatic health status of a subject comprising determining the level of one or more, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or all of miR-26b, -122, 9, -196b, -677, -541, -125b, -500, -466j, -544, -1a-2, -1194, -700, -27a, -192, -214, -377, -1906, -455, -23b, -106a, -200b, -532, -34c, -151, -653, -687, and/or -483, in a sample isolated from the patient wherein up-regulation of one or more of miR-21, -22, -7a, -24, -155, -195, -34a, -1906, 26b, -122, -677, -541, -125b, -500, -466, -544, -1a-2, -1194 and/or -700 and/or one or more of down-regulation of miR-9, -377, -27a, -192, -214, -196b, -455, -23b, -106a, -200b, -532, -34c, -151, -653, -687, and/or -483, identifies the patient as likely to have hepatic disease.

Also provided herein are isolated or purified exosomes isolated from a body fluid (e.g., urine, saliva, lymphatic fluid, breast milk, blood, serum and/or plasma) of a non-diseased subject. In one aspect, the exosomes have a unique molecular profile in that the microRNA (miR) profile of the exosomes comprise the lack of up-regulation of one or both of the markers miR26b and/or -122 and/or the lack of down-regulation of one or more of miR-9 and/or -196b, as compared to the exosome miR profile of a subject that is suffering from a liver or fibrotic disease or an associated disorder.

In a further aspect, the exosomes are further identified by the microRNA (miR) profile by the lack of up-regulation of one or more of miR-7a, -21, -22, -24, -34a, -155, -195, -677, -541, -125b, -122, -155, -195, -1906, -500, -466j, -544, -1a-2, -1194, and/or -700, and/or the lack of down-regulation of miR-27a, -196b, -9, -192, -214, -377, -455, -23b, -106a, -200b, -532, -34c, -151, -653, -687, and/or -483 as compared to the exosome miR profile of a subject that is suffering from a liver or fibrotic disease or an associated disorder.

A kit also is provided for one or more of: a) inhibiting the progression of, b) preventing or c) treating, liver fibrosis or an associated disorder in a subject in need thereof, comprising an effective amount of the isolated or purified exosomes and/or the pharmaceutical composition as described above and/or reagents and/or instructions for use.

Yet further provided is a kit comprising one or more probes and/or primers to determine the expression profile of one or more, two or more, three or more or all four of miR26b, miR-122 miR-9; and/or miR-196b. In a further aspect, the kit independently or in addition also comprises, consists essentially of, or yet further consists of, one or more, two or more, three or more, four or more, five or more, six or more, seven or more, eight or more, nine or more, ten or more, eleven or more, twelve or more, thirteen or more, fourteen or more, fifteen or more, or all (including all integers there between) of miR-7a, -26b, -122, -196b, -9, -21, -22, -24, -34a, -155, -195, -27a, -192, -214, -377, -455, -23b, -106a, -200b, -532, -34c, -151, -653, -687, -483, -1906, -677, -541, -125b, -500, -466j, -544, -1a-2, -1194, and/or -700. In a further aspect, the kit further comprises detectable labels that in one aspect are attached to the probes and/or primers, and wherein in one aspect, wherein the detectable label is not a polynucleotide.

BRIEF DESCRIPTION OF THE DRAWINGS

FIGS. 4A-4E show in vivo effects of exosomes on $CCl_4$-induced fibrotic signals in the liver (short-term injury). Transgenic (TG), Connective Tissue Growth Factor-Green Fluorescent Protein (CTGF-GFP) mice received $CCl_4$ intramuscular (i.m.) (4 μl $CCl_4$ diluted in 26 μl corn oil) over a 7 day period, followed a few hours later by administration of exosomes (100-300 μl; 3 μg/ul) i.p. On Day 9, livers were examined macroscopically (A) followed by resection and analysis for direct green fluorescent protein (GFP) expression (a measure of CTGF promoter activity) (B, C). Total liver RNA was subject to RT-PCR with the finding that $CCl_4$-induced changes in CTGF, αSMA or miR-214 were reversed by exosomes (D). (E) Immunostaining for αSMA. Oil-treated (control) animals show positive staining in smooth muscle cells of vasculature only. $CCl_4$-treated animals show massive activation of HSC, the level of which was strongly attenuated in exosome-treated mice.

FIGS. 5A-5D show in vivo effects of exosomes on CCl4-induced fibrosis in the liver (long-term injury). TG CTGF-GFP mice received $CCl_4$ i.m. over a 5 week period. Some mice also received exosomes by i.p. administration (100-300 μl) on the same day as and for the last 2 weeks of $CCl_4$ (carbon tetrachloride) treatment. Livers were assessed for (A) direct GFP expression (=CTGF promoter activity) (B) expression of CTGF, αSMA, collagen or miR-214 by RT-PCR of total hepatic RNA; and (C, D) Immunostaining for αSMA, CTGF or collagen I. All outcome measures affected by $CCl_4$ were reversed by exosomes.

FIG. 9 is a table identifying some major fibrotic diseases that are provided as examples of "associated disorders."

DETAILED DESCRIPTION

Figures 1A, 1B:
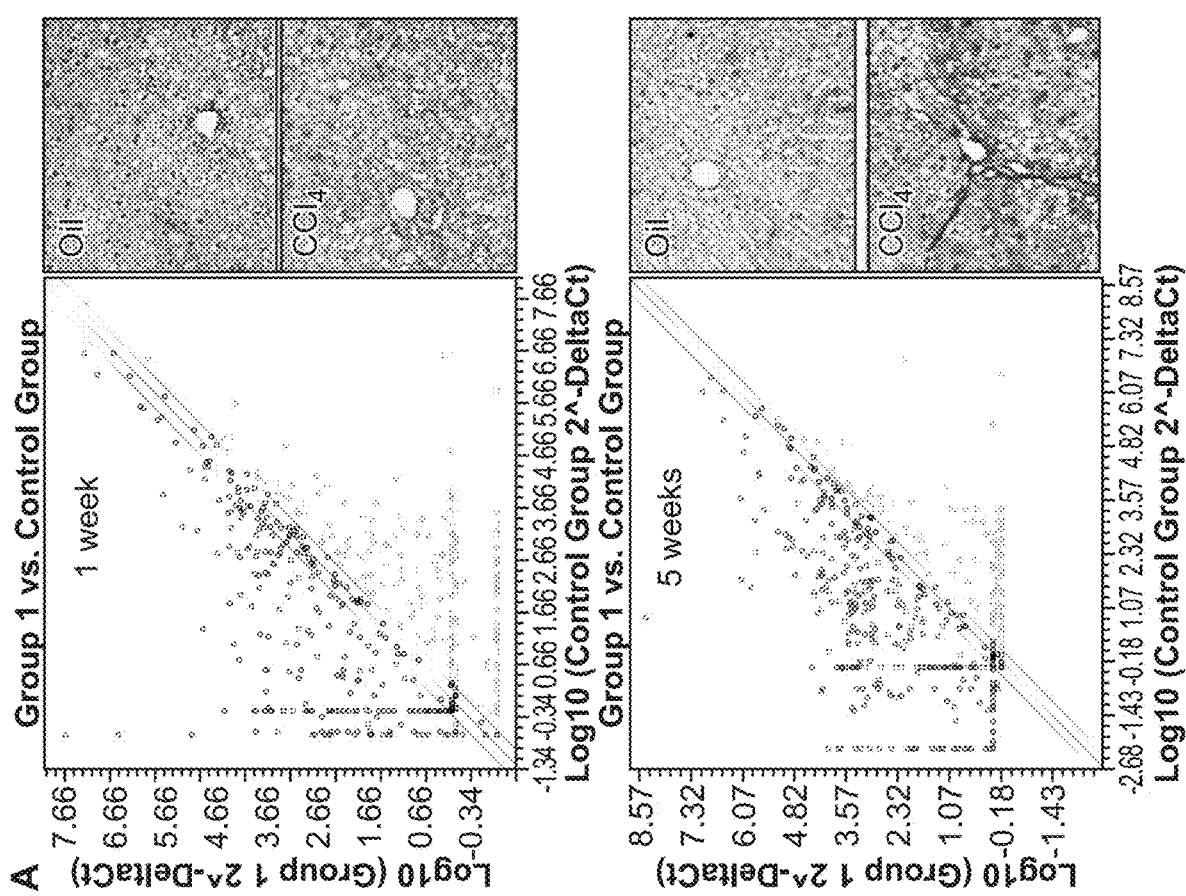
FIGS. 1A-1B show that mice with liver fibrosis have a circulating exosomal miR content that is distinct from that of normal mice. (A) MiRs in circulating exosomes from Balb/c mice treated intraperitoneal (i.p.) with corn oil (30 μl) or carbon tetrachloride ($CCl_4$; 4 μl $CCl_4$ diluted in 26 μl corn oil)) for 1 week or 5 weeks. Profiling was performed on exosomes from 1 ml of pooled serum (5 mice; 200 μl/mouse) using a mouse miRnome miR PCR Array. Left: MiRs outside the outer diagonal lines were up-regulated (red) or down-regulated (green) more than 2-fold in response to $CCl_4$. Right: Sirius red-stained liver sections. (B) RT-PCR analysis of circulating exosomes collected at 1-, 3- or 4 weeks in which miRs were selected based on their expression in (A) and compared to published studies reporting their up- (dark gray; "↑") or down- (light gray; "↓") regulation in fibrotic liver tissues. Exosomal miRs termed "novel" are examples of miRs not previously reported in liver fibrosis but which can have serum exosome biomarker utility in early or late fibrotic injury.

Throughout this disclosure, various publications, patents and published patent specifications are referenced by an identifying citation. The disclosures of these publications, patents and published patent specifications are hereby incorporated by reference into the present disclosure to more fully describe the state of the art to which this disclosure pertains.

The practice of the present disclosure employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook and Russell eds. MOLECULAR CLONING: A LABORATORY MANUAL, 3$^{rd}$ edition (2001); the series CURRENT PROTOCOLS IN MOLECULAR BIOLOGY (F. M. Ausubel et al. eds. (2007)); the series METHODS IN ENZYMOLOGY (Academic Press, Inc., N.Y.); PCR 1: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1999)); CULTURE OF ANIMAL CELLS: A MANUAL OF BASIC TECHNIQUE (R. I. Freshney 5$^{th}$ edition (2005)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); NUCLEIC ACID HYBRIDIZATION (M. L. M. Anderson (1999)); TRANSCRIPTION AND TRANSLATION (B. D. Hames & S. J. Higgins eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); GENE TRANSFER AND EXPRESSION IN MAMMALIAN CELLS (S. C. Makrides ed. (2003)) IMMUNOCHEMICAL METHODS IN CELL AND MOLECULAR BIOLOGY (Mayer and Walker, eds., Academic Press, London (1987)); WEIR'S HANDBOOK OF EXPERIMENTAL IMMUNOLOGY (L. A. Herzenberg et al. eds (1996)).

Definitions

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "exosome" intends a membrane body having an average diameter of from about 10 nm to about 2,000 nm. The term includes microvesicles and exosomes. Microvesicles are also known as circulating microvesicles or microparticles and are fragments of plasma membrane ranging from 100 nm to 1000 nm in approximate diameter shed from almost all cell types. For the purpose of this disclosure and unless specifically noted, the term exosome also includes smaller intracellularly generated extracellular vesicles formed by inward budding of the limiting membranes of multivesicular bodies (MVB) which, upon fusion with the plasma membrane, result in their secretion and deposition into body fluids (e.g., blood, urine). Exosomes contain a complex mixture of microRNAs (miRs), mRNAs and proteins that reflect the transcriptional and translational status of the producer cell. Exosomes are from about 10 to about 250 nm, or alternatively from about 10 to about 200 nm, or alternatively from about 10 to about 175 nm, or alternatively from about 25 to 175 nm, or alternatively from about 40 to about 250 nm, or alternatively from about 40 to about 200 nm, or alternatively from about 50 to 250 nm, or alternatively from about 50 to 200 nm, or alternatively from about 50-150 nm in average diameter. The exosome membranous vesicles arise by inward budding from the limiting membranes of MVB. Upon fusion of MVBs with the plasma membrane, exosomes are liberated from the cells, traverse intercellular spaces, and may be taken up by neighboring cells (Johnstone, R. M. (2006) Blood Cells Mol. Dis. 36(2):315-321; Thery, C. (2011) F1000 Biol. Rep. 3:15; Thery, C. et al. (2002) Nat. Rev. Immunol. 2(8):569-579). Exosomes contain a complex mixture of miRs, mRNAs and proteins and can be isolated from a variety of body fluids as described herein and known in the art.

As used herein, the term "fibrosis" intends the formation of an abnormal amount of insoluble scar tissue as the result of inflammation, irritation, or healing. It is a common and highly debilitating pathology and an end-stage manifestation of diseases such as systemic sclerosis, renal, pulmonary, or cardiac hypertension, myocardial infarction, and chronic liver disease (e.g., hepatitis, alcoholic liver disease, or non-alcoholic steatohepatitis). Numerous studies suggest that fibrosis in different organ systems share common mechanisms including inflammation, a prolonged wound healing response, activation of pro-fibrotic signals, increased matrix deposition and decreased matrix degradation, increased tissue stiffness, and loss of tissue elasticity. Collectively these changes in tissue architecture conspire to cause a loss of normal cell function and viability. Thus anti-fibrotic interventions will likely have utility for antagonizing fibrogenic pathways in a broad variety of fibrotic organ systems, or in tissues undergoing other types of scarring responses.

As used herein, the term "fibrotic disease or condition" intends a pathological condition having symptoms and clinical markers of fibrotic tissue, e.g., systemic sclerosis, renal, pulmonary, or cardiac hypertension, myocardial infarction, and chronic liver disease (e.g., hepatitis, alcoholic liver disease, or non-alcoholic steatohepatitis) and/or in various organs or tissues, e.g., liver, heart, kidney, lung, pancreas, the joints and the eye. Non-limiting examples of fibrotic conditions and associated disorders are provided in FIG. 9 and include without limitation, scleroderma, keloids and rheumatoid arthritis.

As used herein, "a non-diseased subject" intends a subject not diagnosed with a fibrotic disease. In one aspect, the non-diseased subject is one that does not have a clinical diagnosis of hepatic fibrosis and/or liver disease and/or has normal liver function. Clinical parameters for determining if a subject is suffering from a fibrotic disease are known in the art and briefly described herein. Without being limited, exemplary clinical tests for assessing liver function include: serum bilirubin test, serum alkaline phosphatase test, prothrombin time test, alanine transaminase test, aspartate transaminase test, gamma glutamyl transpeptidase test, lactate dehydrogenase test, alpha fetoprotein test, mitochondrial antibody test, and serum α-1 antitrypsin test. Clinical tests for detecting and diagnosing liver fibrosis include without limitation: PGA index, FIB-4 index, Fibrometer, FibroSure, Act-test, SAFE, Heapscore, FibroQ, AAR, APRI, CDS, API, Pohls score, Loks model, liver biopsy, ultrasonography, computed tomography, ultrasound elastography, and magnetic resonance elastography. For example, when the fibrotic condition is liver fibrosis, the above measurements can be combined with approved clinical tests for liver function and/or liver fibrosis.

The term "lack of up-regulation" intends and lack of "down-regulation" intends that the microRNA marker was not determined to be over- or under-expressed as compared to a predetermined value. In one aspect, the predetermined value is a preliminary value from the subject prior to the subsequent measurement (as in prior to therapy) or is a value from a population of subjects that do or do not have clinical manifestation of the related disorder. For example, when the disclosure relates to the treatment of liver fibrosis, a predetermined value can be the average or median exosome miRNA value as measured from a population of subjects that do or do not have a fibrotic or hepatic disease or an associated disorder.

The term "identify" or "identifying" is to associate or affiliate a patient closely to a group or population of patients who likely experience the same or a similar clinical response to treatment.

The terms "protein," "polypeptide" and "peptide" are used interchangeably herein when referring to a gene product.

The term "marker" refers to a clinical or sub-clinical expression of a gene or miRNA of interest.

"Expression" as applied to a gene, refers to the differential production of the miR or mRNA transcribed from the gene or the protein product encoded by the gene. A differentially expressed gene may be over expressed (high expression) or under expressed (low expression) as compared to the expression level of a normal or control cell, a given patient population or with an internal control gene (housekeeping gene). In one aspect, it refers to a differential that is about 1.5 times, or alternatively, about 2.0 times, alternatively, about 2.0 times, alternatively, about 3.0 times, or alternatively, about 5 times, or alternatively, about 10 times, alternatively about 50 times, or yet further alternatively more than about 100 times higher or lower than the expression level detected in a control sample.

In one aspect of the disclosure, a "predetermined threshold level" or "threshold value" is used to categorize expression as high or low. As a non-limiting example of the disclosure, the threshold level of the miR of the exosome is a level of miR expression found in subjects that have been diagnosed with a fibrotic or hepatic disease or an associate disorder. Alternatively or in addition, the predetermined threshold level is the measured miRNA expression level for that individual subject prior to a subsequent measurement, e.g., prior to therapy or prior to an additional dose of the therapy.

In one aspect of the disclosure, miR expression can be provided as a ratio above the threshold level and therefore can be categorized as high expression or up-regulated, whereas a ratio below the threshold level is categorized as down-regulated or low expression.

In another aspect, "expression" level is determined by measuring the expression level of a gene of interest for a given patient population, determining the median expression level of that gene for the population, and comparing the expression level of the same gene for a single patient to the median expression level for the given patient population. For example, if the expression level of a gene of interest for the single patient is determined to be above the median expression level of the patient population, that patient is determined to have high expression (up-regulated) of the gene of interest. Alternatively, if the expression level of a gene of interest for the single patient is determined to be below the median expression level (down-regulated) of the patient population, that patient is determined to have low expression of the gene of interest.

A "internal control" or "housekeeping" gene refers to any constitutively or globally expressed gene whose presence enables an assessment of the expression level of a gene or genes of interest. Such an assessment comprises a determination of the overall constitutive level of gene transcription and a control for variation in sampling error. Examples of such genes include, but are not limited to, RNU6-2, cel-miR-39, SNORD61, SNORD68, SNORD72, SNORD95, SNORD96A, GADPH and/or β-actin.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The phrase "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu, D. Y. et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e., each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "encode" as it is applied to polynucleotides refers to a polynucleotide which is said to "encode" a polypeptide if, in its native state or when manipulated by methods well known to those skilled in the art, it can be transcribed from its gene and/or translated from its mRNA to produce the polypeptide and/or a fragment thereof. The antisense strand is the complement of such a nucleic acid, and the encoding sequence can be deduced therefrom.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein refers to molecules or biological or cellular materials being substantially free from other materials. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

A "blood cell" refers to any of the cells contained in blood. A blood cell is also referred to as an erythrocyte or leukocyte, or a blood corpuscle. Non-limiting examples of blood cells include white blood cells, red blood cells, and platelets.

"Expression" as applied to a gene, refers to the production of the miR or mRNA transcribed from the gene, or the protein product encoded by the mRNA. The expression level of a gene may be determined by measuring the amount of miR or mRNA or protein in a cell or tissue sample. In one aspect, the expression level of a gene is represented by a relative level as compared to a housekeeping gene as an internal control. In another aspect, the expression level of a gene from one sample may be directly compared to the expression level of that gene from a different sample using an internal control to remove the sampling error.

"Overexpression" or "underexpression" refers to increased or decreased expression, or alternatively a differential expression, of a gene in a test sample as compared to the expression level of that gene in the control sample. In one aspect, the test sample is a diseased cell, and the control sample is a normal cell. In another aspect, the test sample is an experimentally manipulated or biologically altered cell, and the control sample is the cell prior to the experimental manipulation or biological alteration. In yet another aspect, the test sample is a sample from a patient, and the control sample is a similar sample from a healthy individual. In a yet further aspect, the test sample is a sample from a patient and the control sample is a similar sample from patient not having the desired clinical outcome. In one aspect, the differential expression is about 1.5 times, or alternatively, about 2.0 times, or alternatively, about 2.0 times, or alternatively, about 3.0 times, or alternatively, about 5 times, or alternatively, about 10 times, or alternatively about 50 times, or yet further alternatively more than about 100 times higher or lower than the expression level detected in the control sample. Alternatively, the gene is referred to as "over expressed" or "under expressed". Alternatively, the gene may also be referred to as "up regulated" or "down regulated".

A "predetermined value" for a gene as used herein, is so chosen that a patient with an expression level of that gene higher than the predetermined value is likely to experience a more or less desirable clinical outcome than patients with expression levels of the same gene lower than the predetermined value, or vice-versa. Expression levels of genes, such as those disclosed in the present disclosure, are associated with clinical outcomes. One of skill in the art can determine a predetermined value for a gene by comparing expression levels of a gene in patients with more desirable clinical outcomes to those with less desirable clinical outcomes. In one aspect, a predetermined value is a gene expression value that best separates patients into a group with more desirable clinical outcomes and a group with less desirable clinical outcomes. Such a gene expression value can be mathematically or statistically determined with methods well known in the art.

Alternatively, a gene expression that is higher than the predetermined value is simply referred to as a "high expression", or a gene expression that is lower than the predetermined value is simply referred to as a "low expression".

Briefly and for the purpose of illustration only, one of skill in the art can determine a predetermined values by comparing expression values of a gene in patients with more desirable clinical parameters to those with less desirable clinical parameters. In one aspect, a predetermined value is a gene expression value that best separates patients into a group with more desirable clinical parameter and a group with less desirable clinical parameter. Such a gene expression value can be mathematically or statistically determined with methods well known in the art.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine," "cytidine," "guanosine," and "thymidine" are used. It is understood that if the nucleic acid is RNA, a nucleotide having a uracil base is uridine.

The terms "oligonucleotide" or "polynucleotide," or "portion," or "segment" thereof refer to a stretch of polynucleotide residues which is long enough to use in PCR or various hybridization procedures to identify or amplify identical or related parts of miR or mRNA or DNA molecules. The polynucleotide compositions of this disclosure include miR, RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

microRNAs, miRNAs, or miRs are single-stranded RNA molecules of that are of various lengths, e.g., from about 15 to about 50 nucleotides, or alternatively from about 19 to about 25 nucleotides in length, which regulate gene expression. miRNAs are encoded by genes from whose DNA they are transcribed but miRNAs are not translated into protein (non-coding RNA); instead each primary transcript (a pre-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

As used herein, a "pre-miRNA" molecule is an RNA molecule of about 100 to about 200 nucleotides, or alternatively from about 100 to about 130 nucleotides which can adopt a secondary structure comprising a double stranded RNA stem and a single stranded RNA loop and further comprises the nucleotide sequence of the miRNA (and its complement sequence) in the double stranded RNA stem. The miRNA and its complement can be located about 10 to about 20 nucleotides from the free ends of the miRNA double stranded RNA stem.

"RNA interference" (RNAi) refers to sequence-specific or gene specific suppression of gene expression (protein synthesis) that is mediated by short interfering RNA (siRNA).

"Short interfering RNA" (siRNA) refers to double-stranded RNA molecules (dsRNA), generally, from about 10 to about 30 nucleotides in length that are capable of mediating RNA interference (RNAi), or 11 nucleotides in length, 12 nucleotides in length, 13 nucleotides in length, 14 nucleotides in length, 15 nucleotides in length, 16 nucleotides in length, 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, or 29 nucleotides in length. As used herein, the term siRNA includes short hairpin RNAs (shRNAs). A siRNA directed to a gene or the mRNA of a gene may be a siRNA that recognizes the mRNA of the gene and directs a RNA-induced silencing complex (RISC) to the mRNA, leading to degradation of the mRNA. A siRNA directed to a gene or the mRNA of a gene may also be a siRNA that recognizes the mRNA and inhibits translation of the mRNA.

"Double stranded RNA" (dsRNA) refer to double stranded RNA molecules that may be of any length and may be cleaved intracellularly into smaller RNA molecules, such as siRNA. In cells that have a competent interferon response, longer dsRNA, such as those longer than about 30 base pair in length, may trigger the interferon response. In other cells that do not have a competent interferon response, dsRNA may be used to trigger specific RNAi.

An "antagomir" is a polynucleotide that is complementary to the miR sequence and, once it binds to and engages the miR, it will prevent the miR from binding its mRNA target.

An mRNA "protector" is a molecule that competes with miR for its binding site on a specific target mRNA moiety. Binding of the protector prevents subsequent binding to the target by the mIR. The activity of the mIR on the specific target gene is thus prevented by the protector which itself is inactive.

When a marker is used as a basis for selecting a patient for a treatment described herein, the marker is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one in the art, measurement of the genetic marker or polymorphism in a clinical setting is a clear indication that this parameter was used as a basis for initiating, continuing, adjusting and/or ceasing administration of the treatments described herein.

The term "treating" as used herein is intended to encompass curing as well as ameliorating at least one symptom of the condition or disease. For example, in the case of liver fibrosis, the term "treatment" intends a more favorable clinical assessment by a treating physician or assistant and/or reduced expression of fibrosis markers, e.g., αSMA, CTGF, collagen, matrix molecules and/or a shift toward normal read-outs in tests that diagnose liver function and/or liver fibrosis.

"An effective amount" intends to indicated the amount of a composition, compound or agent (exosomes) administered or delivered to the subject that is most likely to result in the desired response to treatment. The amount is empirically determined by the patient's clinical parameters including, but not limited to the stage of disease, age, gender and histology.

The term "suitable for a therapy" or "suitably treated with a therapy" shall mean that the patient is likely to exhibit one or more desirable clinical outcome as compared to patients having the same disease and receiving the same therapy but possessing a different characteristic that is under consideration for the purpose of the comparison.

The term "blood" refers to blood which includes all components of blood circulating in a subject including, but not limited to, red blood cells, white blood cells, plasma, clotting factors, small proteins, platelets and/or cryoprecipitate. This is typically the type of blood which is donated when a human patent gives blood.

A "composition" is intended to mean a combination of active exosome or population of exosomes and another compound or composition, inert (e.g., a detectable label or saline) or active (e.g., a therapeutic compound or composition) alone or in combination with a carrier which can in one embodiment be a simple carrier like saline or pharmaceutically acceptable or a solid support as defined below.

A "pharmaceutical composition" is intended to include the combination of an active exosome or population of exosomes with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, the disease being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, inhalation, injection, and topical application.

An agent of the present disclosure can be administered for therapy by any suitable route of administration. It will also be appreciated that the preferred route will vary with the condition and age of the recipient, and the disease being treated.

Modes for Carrying Out the Disclosure

Diagnostic Methods

This disclosure provides diagnostic methods. In one aspect, therapy and a subject's health can be monitored by determining the expression level of one or more, two or more, three or more, or all four of miR-26b, miR-122, miR-9 and/or miR-196b in a sample of exosomes isolated from the subject prior to, during, and/or after the therapy. The method can further comprise, or alternatively consist essentially of, or yet further consist of, determining the expression level of one or more, two or more, three or more, four or more, five or more, six or more, seven or more, eight or more, nine or more, ten or more, eleven or more, twelve or more, thirteen or more, fourteen or more, fifteen or more, or all (including all integers there between) of miR-7a, -21, -26b, -122, -196b, -9, -22, -24, -34a, -155, -195, -27a, -192, -214, -377, -455, -23b, -106a, -200b, -532, -34c, -151, -653, -687, -483, -1906, -677, -541, -125b, -500, -466j, -544, -1a-2, -1194, and/or -700 in a sample of exosomes isolated from the subject.

In one aspect, the exosomes have an average diameter from about 10 to about 250 nm, or alternatively from about 10 to about 200 nm, or alternatively from about 10 to about 175 nm, or alternatively from about 25 to 175 nm, or alternatively from about 40 to about 250 nm, or alternatively from about 40 to about 200 nm, or alternatively from about 50 to 250 nm, or alternatively from about 50 to 200 nm, or alternatively from about 50-150 nm in average diameter. In another aspect, the term exosome also includes microvesicles that range from 100 nm to 1000 nm in approximate diameter.

The measurement of the above-noted miRNA markers can be combined with clinical parameters. Without being limited, exemplary clinical tests for assessing liver function include: serum bilirubin test, serum alkaline phosphatase test, prothrombin time test, alanine transaminase test, aspartate transaminase test, gamma glutamyl transpeptidase test, lactate dehydrogenase test, alpha fetoprotein test, mitochondrial antibody test, and serum a-1 antitrypsin test. Clinical tests for detecting and diagnosing liver fibrosis include without limitation: PGA index, FIB-4 index, Fibrometer, FibroSure, Act-test, SAFE, Heapscore, FibroQ, AAR, APRI, CDS, API, Pohls score, Loks model, liver biopsy, ultrasonography, computed tomography, ultrasound elastography, and magnetic resonance elastography. For example, when the fibrotic condition is liver fibrosis, the above measurements can be combined with approved clinical tests for liver function and/or liver fibrosis.

The method also can be used to determine if a subject is a suitable for the therapy as described herein, by performing the above diagnostic method. When the exosome expression level is up-regulated (high expression) for mi-26b and/or -122 and/or down-regulated for miR-9 and/or -196b, the subject is likely to have a fibrotic disease, a liver or a hepatic disease or an associated disorder, and if the exosome expression is normal or reversed from the above, the subject is not likely to have a fibrotic disease, a liver disease, or hepatic disease or an associated disorder, and therefore therapy is not needed. The method can further comprise determining and correlating the expression level of one or more, two or more, three or more, four or more, five or more, six or more, seven or more, eight or more, nine or more, ten or more, eleven or more, twelve or more, thirteen or more, fourteen or more, fifteen or more, or all (including all integers there between) of miR-7a, -21, -22, -24, -26b, -122, -196b, -9, -34a, -155, -195, -27a, -192, -214, -377, -455, -23b, -106a, -200b, -532, -34c, -151, -653, -687, -483, -1906, -677, -541, -125b, -500, -466j, -544, -1a-2, -1194, and/or -700 in a sample of exosomes isolated from the subject, and wherein high levels of one or more of miR-26b, -21, -22, -7a, -24, -155, -195, -34a, -1906, -122, -677, -541, -125b, -500, -466, -544, -1a-2, -1194 and/or -700, and one or more of low levels of miR-9, -377, -27a, -192, -214, -196b, -455, -23b, -106a, -200b, -532, -34c, -151, -653, -687, and/or -483, identifies the patient as likely to have fibrotic disease, a liver or a hepatic disease and in need of therapy. If the subject is in need of therapy, the compositions of this disclosure, alone or in combination with other known therapies, can then be administered to the subject in need of treatment. The diagnostic methods can be repeated throughout and after therapy to monitor the subject's health status and the efficacy of the therapy.

The therapy and patient's health can be monitored by determining the level of one or more, two or more, three or more, or all of miR-26b, -122, miR-9 and/or -196b in a sample isolated from the patient prior to, during and after the therapy. In a further aspect, the therapy and patient's health and therapy response can be monitored by determining the level of one or more, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or all of (and integers there between) of miR-26b, -122, -9, -196b, -677, -541, -125b, -500, -466j, -544, -1a-2, -1194, -700, -27a, -192, -214, -377, -1906, -455, -23b, -106a, -200b, -532, -34c, -151, -653, -687, -21, -22, -7a, -24, -155, -195, -34a, and/or -483, in a sample isolated from the patient prior to, during and after the therapy and wherein high levels of one or more of miR-26b, -21, -22, -7a, -24, -155, -95, -34a, -1906, -122, -677, -541, -125b, -500, -466, -544, -1a-2, -1194 and/or -700, and one or more of low levels of miR-9, -196b, -455, -23b, -106a, -200b, -532, -34c, -151, -653, -687, -377, -27a, -192, -214, and/or -483, identifies the patient as likely to have fibrotic disease, a liver or a hepatic disease.

In one aspect, this disclosure also provides determining the hepatic health status of a subject comprising determining the level of one or more, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or all of (an integers there between) of miR-26b, -122, -9, -196b, -677, -541, -125b, -500, -466j, -544, -1a-2, -1194, -700, -27a, -192, -214, -377, -1906, -455, -23b, -106a, -200b, -532, -34c, -151, -653, -687, -21, -22, -7a, -24, -155, -195, -34a and/or -483, in a sample isolated from the patient wherein up-regulation of one or more of miR-26b, -122, -677, -541, -125b, -500, -466, -544, -1a-2, -1194, -21, -22, -7a, -24, -155, -195, -34a, -1906, and/or -700, and/or one or more of down-regulation of miR-9, -377, -27a, -192, -214, -196b, -455, -23b, -106a, -200b, -532, -34c, -151, -653, -687, and/or -483, identifies the patient as likely to have fibrotic disease, a liver or a hepatic disease.

Measurement of expression level or activity level can be accomplished by methods known in the art and briefly described herein, e.g., by PCR, qPCR, miRNA arrays, RNA-seq, multiplex miRNA profiling. The tools and methodologies are known in the art and commercially available, from Abcam (see abcam.com, last accessed Sep. 25, 2015).

The measurement can be compared to suitable controls, e.g., a prior measurement for that subject or a suitable internal control.

Collection of samples of exosomes from body fluid, e.g., urine, blood, saliva, breast milk, lymphatic fluid, serum or plasma can be done with methods known in the art and described briefly herein. The exosomes can be purified from the fluid using the methods disclosed herein in art-recognized methods, such as by ultracentrifugation as described by Thery et al. (2006) "Isolation and characterization of exosomes from cell culture supernatants and biological fluids" Curr. Protoc. Cell Biol., Chapter 3, or as disclosed in Hong et al. (2014) PLoS One 9(8):e103310, doe:10,1371 and Jayachandran et al. (2012) J. Immun. Methods, 375: 207-214. Commercial kits also are available, e.g., PureExo (101BIO, Palo Alto Calif., for serum and plasma), Exo MIR Plus (Bioo Scientific, Austin Tex., USA), ExoQuick (SBI, Mountain View, Calif., USA, for tissue culture) and Exo-Spin Kit (Cell Guidance Systems, Carlsbad Calif., USA). As apparent to the skilled artisan, the isolation method will depend on the size and composition of the exosome to be isolated. As an example, ultracentrifugation can be used but for larger microvesicles, and the speed shall not exceed about 70,000 g or alternatively about 60,000 g. Alternatively, ultracentrifugation is used for smaller exosomes, but being much smaller, speeds of 90,000 or alternatively of 100,000 g or more are needed.

The methods are useful in the diagnosis of a subject, e.g., a mammal, an animal, or yet further a human patient. For the purpose of illustration only, a mammal includes but is not limited to a human, a simian, a murine, a rat, a bovine, a canine, a feline, an equine, a porcine or an ovine.

Compositions

Provided herein is a purified or isolated population of exosomes isolated from a body fluid of a non-diseased subject. In one aspect, the exosomes have an average diameter from about 10 to about 250 nm, or alternatively from about 10 to about 200 nm, or alternatively from about 10 to about 175 nm, or alternatively from about 25 to 175 nm, or alternatively from about 40 to about 250 nm, or alternatively from about 40 to about 200 nm, or alternatively from about 50 to 250 nm, or alternatively from about 50 to 200 nm, or alternatively from about 50-150 nm in average diameter. In another aspect, the term exosome also includes microvesicles that range from 100 nm to 1000 nm in approximate diameter. Methods to isolated and characterize the exosomes are known in the art (see Rekker et al. (2014) "Comparison of serum exosome isolation methods for miroRNA profiling" Clin. Biochem. 47(102):135-138) and briefly described herein.

In an alternate aspect, the compositions can comprise, or alternatively consist essentially of, or yet further consist of, one or more, two or more, three or more, four or more, five or more, six or more, seven or more, eight or more, nine or more, ten or more, eleven or more, twelve or more, thirteen or more, fourteen or more, fifteen or more, sixteen or more, or alternatively all of miR-9, -196b, -27a, -192, -214, -377, -455, -23b, -106a, -200b, -532, -34c, -151, -653, -687, and/or -483 and/or polynucleotides that encode them. The polynucleotides can be inserted into an appropriate expression vector and delivered using techniques known in the art.

Also provided herein are compositions that interfere with or inhibit the fibrotic activity of miRNA, e.g., one or more two or more, three or more, four or more, five or more, six or more, seven or more, eight or more, nine or more, ten or more, eleven or more, twelve or more, thirteen or more, fourteen or more, fifteen or more, sixteen or more, or alternatively all of (and integers there between) of miRs -21, -22, -7a, -24, -155, -195, -34a, -26b, -122, -1906, -677, -541, -125b, -500, -466j, -544, -1a-2, -1194, and -700 because the exosome levels of these are elevated in fibrosis and they thus could contribute to driving the fibrotic response. These agents include, for example inhibitory RNA, an antagomir, and/or a protectors, and/or the polynucleotides that encode them, that are specific to the listed miRs. These can be combined with one or more, two or more, three or more, four or more, five or more, six or more, seven or more, eight or more, nine or more, ten or more, eleven or more, twelve or more, thirteen or more, fourteen or more, fifteen or more, sixteen or more, or alternatively all of miR-9, -196b, miR-27a, -192, -214, -377, -455, -23b, -106a, -200b, -532, -34c, -151, -653, -687, and/or -483 and/or polynucleotides that encode them. The polynucleotides can be inserted into an appropriate expression vector and delivered using techniques known in the art.

These compositions are useful for the treatment of disease, such as fibrotic disease, a liver or a hepatic disease and associated disorders.

miRNA, inhibitory RNA, antagomirs, and protectors can be prepared by any appropriate method, e.g., by isolation form natural products such as exosomes or recombinantly produced, for example, by a chemical synthetic method or a method using genetic recombination technique. When the production is carried out by a method using genetic recombination technique, miRNA can, for example, be produced through a transcription reaction with use of a DNA template and a RNA polymerase obtained by means of gene recombination. Examples of suitable RNA polymerase include a T7 RNA polymerase, a T3 RNA polymerase, and a SP6 RNA polymerase. They can be produced in a eukaryotic or prokaryotic cells, e.g., *E. coli* or other bacteria, yeast, mammalian, human, murine or simian for example.

In some aspects, the miRNAs are contained in or encoded by other nucleic acid molecules, and it is these nucleic acids that are isolated and purified for use in the described methods. The miRNAs can be contained within larger RNA molecules which, when processed, produce the miRNAs described herein. In another example, the miRNAs are encoded by nucleic acid molecules, which may be contained, for example, in vectors. Thus, also provided herein are vectors that contain nucleic acid that encodes the miRNAs.

In some instances, the miRNAs or nucleic acids encoding the miRNA are produced synthetically using well-known methods or are isolated from cells or tissues. Typically, the miRNAs or nucleic acid molecules containing or encoding the miRNAs are obtained using genetic engineering techniques to produce a recombinant nucleic acid molecule, which can then be isolated or purified by techniques well known to one of ordinary skill in the art. In these recombinant methods, nucleic acid encoding the miRNA is cloned into an appropriate expression vector. It is well within the skill of a skilled artisan to design DNA that encodes a miRNA provided herein.

Any suitable host/vector system can be used to express one or more of the miRNAs described herein. It is well with the skill of those in the art to select an appropriate system based on, for example, whether the miRNA or nucleic acid molecule encoding the miRNA is being isolated and purified for subsequent use, and/or whether the miRNA will be expressed in vivo following administration to a subject.

In particular examples, the miRNAs described herein (including precursor miRNAs) are encoded by vectors for expression of the miRNA in vivo following administration of the vector to a subject. The choice of vector, including the particular regulatory elements contained in the vector for expression of heterologous nucleic acid, can be influenced by the cell type to which the vector is being targeted, and such selection is well within the level of skill of the skilled artisan. For example, the nucleic acid encoding the miRNA can be under the control of a tissue- or cell-specific promoter, such that the miRNA is only expressed in that particular tissue or cell type. Tissue- or cell-specific promoters are well known in the art.

In further examples, the nucleic acid encoding the miRNA is cloned into a viral vector, including, but not limited to, retroviral, adenoviral, lentiviral and adeno-associated viral vectors. Although viral vectors can be replication incompetent or replication competent, for subsequent use in therapeutic applications, typically replication incompetent vectors are selected.

The activity of the miRNAs can be assessed using in vitro assays and animal models well known to those skilled in the art. The miRNAs also can be assessed in human clinical trials under appropriate supervision.

In one aspect, the non-diseased subject is one that is not suffering from liver or a fibrotic disease or an associated disorder. In another aspect, the exosomes have a microRNA (miR) profile comprising, or alternatively consisting essentially of, or yet further consisting of, lack of up-regulation of one or both of the markers miR-26b and/or -122, as compared to the miR profile of a subject that is suffering from liver or a fibrotic disease or an associated disorder.

Also provided is a purified or isolated population of exosomes isolated from a body fluid of a non-diseased subject, wherein the microRNA (miR) profile of the exosomes comprises, or alternatively consist essentially of, or yet further consist of, lack of down-regulation of one or both of miR-9 and/or -196b, as compared to the miR profile of a subject that is suffering from liver or a fibrotic disease or an associated disorder.

Further provided is a purified or isolated population of exosomes isolated from a body fluid of a non-diseased subject, wherein the microRNA (miR) profile of the exosomes comprises lack of up-regulation of one or both of the markers miR-26b and/or -122 and/or lack of down-regulation of one or both of miR-9 and/or -196b, as compared to the miR profile of a subject that is suffering from liver or a fibrotic disease or an associated disorder.

In one aspect, the purified or isolated population of exosomes further comprise lack of up-regulation or low expression of one or more, two or more, three or more, four or more, five or more, six or more, seven or more, eight or more, nine or more, ten or more, eleven or more, twelve or more, thirteen or more, fourteen or more, fifteen or more, or all (including all integers there between) of miR-7a, -21, -22, -24, -34a, -155, -195, -677, -541, -125b, -500, -466j, -544, -1a-2, -1194, -1906, -26b, -122 and/or -700 and/or lack of down-regulation or high expression of one or more, two or more, three or more, four or more, five or more, six or more, seven or more, eight or more, nine or more, ten or more, eleven or more, twelve or more, or all of miR-27a, -192, -214, -377, -455, -23b, -9, -106a, -200b, -196b, -532, -34c, -151, -653, -687, and/or -483.

The purified or isolated population of exosomes are isolated or purified from a body fluid selected from the group of urine, lymphatic fluid, breast milk, saliva, blood, serum and/or plasma. The exosomes can be isolated from more than one source and combined or alternatively maintained as a tissue-specific sample.

This disclosure also provides pharmaceutical compositions comprising, or consisting essentially of, or yet further consisting of, purified or isolated exosomes and/or miRNA as described above. In one aspect, the pharmaceutical composition comprises, or alternatively consists essentially of, or yet further consists of, a pharmaceutically acceptable carrier and an effective amount of these exosomes isolated from a body fluid of a non-diseased subject. Non-limiting examples of carriers include phosphate buffered saline (PBS), saline or a biocompatible matrix material such as a collagen matrix or a decellularized liver matrix (DCM as disclosed in Wang et al. (2014) J. Biomed. Mater Res. A. 102(4):1017-1025) for topical or local administration. The compositions can optionally contain a protease inhibitor, glycerol and/or dimethyl sulfoxide (DMSO). They can be further formulated in liposomes or micelles, using methods known in the art.

For each of the above compositions, the fluid from which the exosomes are isolated or purified is selected from the group of urine, breast milk, lymphatic fluid, saliva, blood, serum or plasma and can be present in a variety of concentrations.

The pharmaceutically acceptable carrier comprises one or more of a biocompatible matrix or a liquid carrier, The pharmaceutical compositions of this disclosure can be formulated for freeze-drying or lyophilisation using methods known in the art.

The pharmaceutical composition are intended for in vitro and in vivo use. The compositions can comprise a concentration of exosomes and/or miRNA and/or inhibitory molecules (as measured by exosomal protein content (measured by Bicinchoninic protein assay (BCA), commercially available from Bio-Rad or Pierce Biotechnology, Inc., for example) from about 1 mg/ml to about 10 mg/ml, or alternatively from about 1 to about 8 mg/ml, or alternatively from 2 to about 8 mg/ml, or alternatively from 2 to about 5 mg/ml, or about 2 to 4 mg/ml, or alternatively from 3 mg/ml to 20 mg/ml When administered to the subject, an effective amount of the exosomes are administered to the subject, to cause at least about 75%, or alternatively at least about 80%, or alternatively at least about 85%, or alternatively at least about 90%, or alternatively at least about 95%, or alternatively at least about 99% effectiveness in the methods provided herein as compared to a control that does not receive the composition. Comparative effectiveness can be determined by suitable in vitro or in vivo methods as known in the art and briefly exemplified herein.

In one aspect, the compositions are pharmaceutical formulations for use in the therapeutic methods of this disclosure and for the treatment of the appropriate or relevant disease. While the examples are noted for the treatment of hepatic disease, the principles can be applied to other disease conditions, including fibrotic disease in other organ or tissue as noted above. In the context of this disclosure when the exosomes and/or miRNA are isolated from a subject that is not suffering from a fibrotic or hepatic disease or an associated disorder, the exosomes are useful for treating a subject having the disease. When the exosomes and/or miRNA are isolated from a subject that is not suffering from a cardiac fibrotic disease or an associated disorder, the exosomes are useful for treating a subject having the cardiac fibrotic disease or an associated disorder.

In a further aspect, the disclosure provides a pharmaceutical composition comprising, or alternatively consisting essentially of, or yet further consisting of, the isolated or purified exosomes in a concentration such that composition comprises at least 75%, or alternatively at least 80%, or alternatively at least 85%, or alternatively at least 90%, or alternatively at least 95% or alternatively at least 97%, or alternatively at least 98%, or alternatively, at least 99% of exosomes (% noted as mg of exosomes and/or miRNA per mg of total proteins) in the total composition.

Therapeutic Methods

The compositions are useful for the preparation of a medicament and/or to perform methods for one or more of: a) inhibiting the progression of, b) preventing or c) treating, a disease, e.g., a fibrotic disease or an associated disorder. As noted above, the exosomes are selected and purified from the body fluid of a patient that does not have the disease or disorder to be treated. In addition or alternatively, RNA polynucleotides and/or DNA that encodes them are isolated or chemically or recombinantly produced. In one aspect, the exosomes previously have been isolated from the subject prior to disease diagnosis. For example, a patient may be at risk for a disease, e.g., liver disease, and the exosomes are isolated and processed for storage (at for example, in an appropriate solvent such as glycerol and DMSO, at from about −70° C. to -90° C. or alternatively about −80° C.)

In one aspect, the compositions are useful for the preparation of a medicament and/or to perform methods for one or more of: a) inhibiting the progression of, b) preventing or c) treating, liver fibrosis or an associated disorder in a subject in need thereof. The methods comprise, or alternatively consist essentially of, or yet further consist of, administering to the subject an effective amount of the pharmaceutical composition described above. Non-limiting examples of "an associated disorder" include the group of: inflammation of the liver, high deposition of lipids, high deposition of insoluble collagen, high deposition of extracellular matrix components, cirrhosis, hepatocarcinoma, end-stage liver disease. These conditions are well known in the art and can be diagnosed by a treating physician.

The therapy and patient's health can be monitored using the diagnostic methods disclosed herein. A non-limiting example of such is by determining the level of one, or two or more, three or more, or all of miR-26b or -122, miR-9, or -196b in a sample isolated from the patient prior to, during and after the therapy. In one aspect, this disclosure also provides determining the liver or hepatic health status of a subject by determining the level of one or more or two or more of miR-26b or -122, miR-9, and/or -196b in a sample isolated from the subject, lack of down-regulation (e.g., normal or up-regulation) of one or more of these markers identifies the patient as not likely to have hepatic disease and down-regulation of these markers identifies the subject as likely to have liver fibrosis or an associated disease.

The therapy and patient's health can be monitored by determining the level of one or more, two or more, three or more, or all of miR-26b, -122, miR-9 and/or -196b in a sample isolated from the patient prior to, during and after the therapy. In a further aspect, the therapy and patient's health and therapy response can be monitored by determining the level of one or more, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or all of (and integers there between) of miR-26b, -122, -9, -196b, -677, -541, -125b, -500, -466j, -544, -1a-2, -1194, -700, -27a, -21, -22, -7a, -24, -155, -195, -34a, -192, -214, -377, -1906, -455, -23b, -106a, -200b, -532, -34c, -151, -653, -687, and/or -483, in a sample isolated from the patient prior to, during and after the therapy and wherein high levels of one or more of miR-26b, -122, -677, -541, -125b, -500, -466, -21, -22, -7a, -24, -155, -195, -34a, -1906, -544, -1a-2, -1194 and/or -700, and one or more of low levels of miR-9, -377, -27a, -192, -214, -196b, -455, -23b, -106a, -200b, -532, -34c, -151, -653, -687, and/or -483, identifies the patient as likely to have fibrotic or hepatic disease.

In one aspect, this disclosure also provides determining the health status, e.g., hepatic health status of a subject comprising determining the level of one or more, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or all of (and integers there between) of miR-26b, -122, -9, -196b, -677, -541, -125b, -500, -466j, -544, -1a-2, -1194, -700, -27a, -21, -22, -7a, -24, -155, -195, -34a, -192, -214, -377, -1906, -455, -23b, -106a, -200b, -532, -34c, -151, -653, -687, and/or -483, in a sample isolated from the patient prior to, during and after the therapy and wherein high levels of one or more of miR-26b, -122, -677, -541, -125b, -500, -466, -21, -22, -7a, -24, -155, -195, -34a, -1906, -544, -1a-2, -1194 and/or -700, and one or more of low levels of miR-9, -377, -27a, -192, -214, -196b, -455, -23b, -106a, -200b, -532, -34c, -151, -653, -687, and/or -483, identifies the patient as likely to have fibrotic or hepatic disease.

The compositions can then be administered to subjects identified as likely to have fibrosis, liver fibrosis, hepatic disease or an associated disorder. In these methods, the exosomes are allogeneic or autologous to the subject receiving the exosomes.

As noted, the composition is administered in an effective amount. For example, an effective amount comprises from about 1 to about 1,000 mg/kg, or alternatively from about 1 to about 500 mg/kg, or alternatively from about 5 to about 500 mg/kg, or alternatively from about 10 to about 100 mg/kg, or alternatively from about 5 mg/kg to about 100 mg/kg, or alternatively from about 10 mg/kg to about 80 mg/kg, or alternatively from about 10 mg/kg to about 50 mg/kg, or alternatively from about 15 mg/kg to about 50 mg/kg, or alternatively more than 5 mg/kg, or alternatively more than about 10 mg/kg, or alternatively more than about 15 mg/kg, or alternatively more than about 20 mg/kg, or alternatively more than 25 mg/kg, or alternatively more than 30 mg/kg, each as measured per kg of body weight of the subject. The effective amount is in one aspect, per dose, or as a daily dose, or alternatively the total over the course of treatment.

The compositions can be administered by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. Non-limiting examples of carriers include phosphate buffered saline (PBS), saline or a biocompatible matrix material such as a decellularized liver matrix (DCM as disclosed in Wang et al. (2014) J. Biomed. Mater Res. A. 102(4):1017-1025) for topical or local administration. The compositions can optionally contain a protease inhibitor, glycerol and/or dimethyl sulfoxide (DMSO).

The pharmaceutical compositions can be conveniently presented in dosage unit form and can be prepared by any of the methods well known in the art of pharmacy. The pharmaceutical compositions can be, for example, prepared by uniformly and intimately bringing the active ingredient into association with a liquid carrier, a finely divided solid carrier or both, and then, if necessary, shaping the product into the desired formulation. In the pharmaceutical composition the active object compound is included in an amount sufficient to produce the desired therapeutic effect. For example, pharmaceutical compositions of the disclosure may take a form suitable for virtually any mode of administration, including, for example, topical, ocular, oral, buccal, systemic, nasal, injection, transdermal, rectal, and vaginal, or a form suitable for administration by inhalation or insufflation.

Systemic formulations include those designed for administration by injection (e.g., subcutaneous, intravenous, intramuscular, intrathecal, or intraperitoneal injection) as well as those designed for transdermal, transmucosal, oral, or pulmonary administration.

Useful injectable preparations include sterile suspensions, solutions, or emulsions of the active compound(s) in aqueous or oily vehicles. The compositions may also contain formulating agents, such as suspending, stabilizing, and/or dispersing agents. The formulations for injection can be presented in unit dosage form, e.g., in ampules or in multidose containers, and may contain added preservatives.

Alternatively, the injectable formulation can be provided in powder form for reconstitution with a suitable vehicle, including but not limited to sterile pyrogen free water, buffer, and dextrose solution, before use. To this end, the active compound(s) can be dried by any art-known technique, such as lyophilisation, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets, or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets can be coated by methods well known in the art with, for example, sugars, films, or enteric coatings. Additionally, the pharmaceutical compositions containing the 2,4-substituted pyridinediamine as active ingredient or prodrug thereof in a form suitable for oral use may also include, for example, troches, lozenges, aqueous, or oily suspensions, dispersible powders or granules, emulsions, hard or soft capsules, or syrups or elixirs.

Compositions intended for oral use can be prepared according to any method known to the art for the manufacture of pharmaceutical compositions, and such compositions may contain one or more agents selected from the group consisting of sweetening agents, flavoring agents, coloring agents, and preserving agents in order to provide pharmaceutically elegant and palatable preparations. Tablets contain the active ingredient (including drug and/or prodrug) in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch or alginic acid); binding agents (e.g., starch, gelatin, or acacia); and lubricating agents (e.g., magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques described in the U.S. Pat. Nos. 4,256,108; 4,166,452; and 4,265,874 to form osmotic therapeutic tablets for control release. The pharmaceutical compositions of the disclosure may also be in the form of oil-in-water emulsions.

Liquid preparations for oral administration may take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin, or acacia); non-aqueous vehicles (e.g., almond oil, oily esters, ethyl alcohol, Cremophore™, or fractionated vegetable oils); and preservatives (e.g., methyl or propyl-p-hydroxybenzoates or sorbic acid). The preparations may also contain buffer salts, preservatives, flavoring, coloring, and sweetening agents as appropriate.

Preparations for oral administration can be suitably formulated to give controlled release or sustained release of the active compound, as is well known. The sustained release formulations of this disclosure are preferably in the form of a compressed tablet comprising an intimate mixture of compound of the disclosure and a partially neutralized pH-dependent binder that controls the rate of compound dissolution in aqueous media across the range of pH in the stomach (typically approximately 2) and in the intestine (typically approximately about 5.5).

To provide for a sustained release of the exosomes, one or more pH-dependent binders can be chosen to control the dissolution profile of the sustained release formulation so that the formulation releases compound slowly and continuously as the formulation is passed through the stomach and gastrointestinal tract. Accordingly, the pH-dependent binders suitable for use in this disclosure are those which inhibit exosome breakdown and/or release of its contents during its residence in the stomach (where the pH is-below about 4.5), and which promotes the release of a therapeutic amount of the compound of the disclosure from the dosage form in the lower gastrointestinal tract (where the pH is generally greater than about 4.5). Many materials known in the pharmaceutical art as "enteric" binders and coating agents have a desired pH dissolution properties. The examples include phthalic acid derivatives such as the phthalic acid derivatives of vinyl polymers and copolymers, hydroxyalkylcelluloses, alkylcelluloses, cellulose acetates, hydroxyalkylcellulose acetates, cellulose ethers, alkylcellulose acetates, and the partial esters thereof, and polymers and copolymers of lower alkyl acrylic acids and lower alkyl acrylates, and the partial esters thereof. One or more pH-dependent binders present in the sustained release formulation of the disclosure are in an amount ranging from about 1 to about 20 wt %, more preferably from about 5 to about 12 wt % and most preferably about 10 wt %.

One or more pH-independent binders may be in used in oral sustained release formulation of the disclosure. The pH-independent binders can be present in the formulation of this disclosure in an amount ranging from about 1 to about 10 wt %, and preferably in amount ranging from about 1 to about 3 wt % and most preferably about 2.0 wt %.

The sustained release formulation of the disclosure may also contain pharmaceutical excipients intimately admixed with the compound and the pH-dependent binder. Pharmaceutically acceptable excipients may include, for example, pH-independent binders or film-forming agents such as hydroxypropyl methylcellulose, hydroxypropyl cellulose, methylcellulose, polyvinylpyrrolidone, neutral poly(meth) acrylate esters, starch, gelatin, sugars, carboxymethylcellulose, and the like. Other useful pharmaceutical excipients include diluents such as lactose, mannitol, dry starch, microcrystalline cellulose and the like; surface active agents such as polyoxyethylene sorbitan esters, sorbitan esters and the like; and coloring agents and flavoring agents. Lubricants (such as talc and magnesium stearate) and other tableting aids can also be optionally present.

The pharmaceutical compositions can be in the form of a sterile injectable aqueous or oleaginous suspension. This suspension can be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that can be employed are water, Ringer's solution, and isotonic sodium chloride solution. The compositions may also be administered in the form of suppositories for rectal or urethral administration of the drug.

For topical use, creams, ointments, jellies, gels, solutions, suspensions, etc., containing the compounds of the disclosure, can be employed. In some embodiments, the compounds of the disclosure can be formulated for topical administration with polyethylene glycol (PEG). These formulations may optionally comprise additional pharmaceutically acceptable ingredients such as diluents, stabilizers, and/or adjuvants.

Included among the devices which can be used to administer compounds of the disclosure, are those well-known in the art, such as metered dose inhalers, liquid nebulizers, dry powder inhalers, sprayers, thermal vaporizers, and the like. Other suitable technology for administration of particular compounds of the disclosure, includes electrohydrodynamic aerosolizers. As those skilled in the art will recognize, the formulation of compounds, the quantity of the formulation delivered, and the duration of administration of a single dose depend on the type of inhalation device employed as well as other factors. For some aerosol delivery systems, such as nebulizers, the frequency of administration and length of time for which the system is activated will depend mainly on the concentration of compounds in the aerosol. For example, shorter periods of administration can be used at higher concentrations of compounds in the nebulizer solution. Devices such as metered dose inhalers can produce higher aerosol concentrations and can be operated for shorter periods to deliver the desired amount of compounds in some embodiments. Devices such as dry powder inhalers deliver active agent until a given charge of agent is expelled from the device. In this type of inhaler, the amount of compounds in a given quantity of the powder determines the dose delivered in a single administration.

Formulations of compounds of the disclosure for administration from a dry powder inhaler may typically include a finely divided dry powder containing compounds, but the powder can also include a bulking agent, buffer, carrier, excipient, another additive, or the like. Additives can be included in a dry powder formulation of compounds of the disclosure, for example, to dilute the powder as required for delivery from the particular powder inhaler, to facilitate processing of the formulation, to provide advantageous powder properties to the formulation, to facilitate dispersion of the powder from the inhalation device, to stabilize to the formulation (e.g., antioxidants or buffers), to provide taste to the formulation, or the like. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; and the like.

For prolonged delivery, the exosome compositions can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives (e.g., as a sparingly soluble salt). Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in, for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device can be accompanied by instructions for administration.

The compositions will generally be used in an amount effective to achieve the intended result, for example, in an amount effective to treat or prevent the particular condition being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

The amount of compound administered will depend upon a variety of factors, including, for example, the particular condition being treated, the mode of administration, the severity of the condition being treated, the age and weight of the patient, the bioavailability of the particular active compound. Determination of an effective dosage is well within the capabilities of those skilled in the art. As known by those of skill in the art, the preferred dosage of compounds of the disclosure will also depend on the age, weight, general health, and severity of the condition of the individual being treated. Dosage may also need to be tailored to the sex of the individual and/or the lung capacity of the individual, where administered by inhalation. Dosage, and frequency of administration of the compositions will also depend on whether the compositions are formulated for treatment of acute episodes of a condition or for the prophylactic treatment of a disorder. A skilled practitioner will be able to determine the optimal dose for a particular individual.

For prophylactic administration, the compound can be administered to a patient at risk of developing one of the previously described conditions. For example, if it is unknown whether a patient is allergic to a particular drug, the compound can be administered prior to administration of the drug to avoid or ameliorate an allergic response to the drug. Alternatively, prophylactic administration can be applied to avoid the onset of symptoms in a patient diagnosed with the underlying disorder.

Effective dosages can be estimated initially from in vitro assays. For example, an initial dosage for use in animals can be formulated to achieve a therapeutic concentration and/or dosage of the exosome composition, as measured in an in vitro assay. Calculating dosages to achieve such effective dosages for other animal models or human patients is well within the capabilities of skilled artisans. For guidance, the reader is referred to Fingl & Woodbury, "General Principles," In: *Goodman and Gilman's The Pharmaceutical Basis of Therapeutics*, Chapter 1, pp. 1-46, latest edition, Pergamagon Press, and the references cited therein.

Initial dosages can also be estimated from in vivo data, such as animal models. Animal models useful for testing the efficacy of compounds to treat or prevent the various diseases described above are well-known in the art. Ordinarily skilled artisans can routinely adapt such information to determine dosages suitable for human administration.

Dosage amounts will typically be in the range of from about 0.0001 or 0.001 or 0.01 mg/kg/day to about 1000 mg/kg/day, but can be higher or lower, depending upon, among other factors, the activity of the composition, its bioavailability, the mode of administration, and various factors discussed above. Dosage amount and interval can be adjusted individually to provide local and/or systemic concentration of the exosomes that are sufficient to maintain therapeutic or prophylactic effect. For example, the compositions can be administered once per week, several times per week (e.g., every other day), once per day, or multiple times per day, depending upon, among other things, the mode of administration, the specific indication being treated, and the judgment of the prescribing physician. Skilled artisans will be able to optimize effective local dosages without undue experimentation.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

Kits

Also provided are kits for administration of the compositions and carrying out the diagnostic methods comprising the composition that may include an appropriate dosage amount. Kits may further comprise suitable packaging and/or instructions for use of the compositions and/or diagnostic methods. Kits may also comprise a means for the delivery of the at least one compositions and a device such as an inhaler, spray dispenser (e.g., nasal spray), syringe for injection, or pressure pack for capsules, tables, suppositories, or other device as described herein.

In one aspect, a kit comprising one or more probes and/or primers to determine the expression profile of one or more, two or more, three or more or all four of miR26b, miR-122 miR-9; and/or miR-196b. In a further aspect, the kit also comprises one or more, two or more, three or more, four or more, five or more, six or more, seven or more, eight or more, nine or more, ten or more, eleven or more, twelve or more, thirteen or more, fourteen or more, fifteen or more, or all (including all integers there between) of miR-26b, -122, -9, -196b, -677, -541, -125b, -500, -466j, -544, -1a-2, -1194, -700, -27a, -21, -22, -7a, -24, -155, -195, -34a, -192, -214, -377, -1906, -455, -23b, -106a, -200b, -532, -34c, -151, -653, -687, and/or -483.

In a further aspect, the kit further comprises detectable labels that in one aspect are attached to the probes and/or primers, wherein in one aspect, the detectable label is not a polynucleotide.

Additionally, the kits can contain the composition and reagents to prepare a composition for administration. The composition can be in a dry or lyophilized form or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to, syringe, pipette, transdermal patch, or inhalant.

The kits may include other therapeutic compounds for use in conjunction with the compounds described herein and as such, the methods as disclosed herein can contain other appropriate therapeutic compounds or agents. These compounds can be provided in a separate form or mixed with the compositions of the present disclosure. The kits will include appropriate instructions for preparation and administration of the composition, side effects of the compositions, and any other relevant information. The instructions can be in any suitable format, including, but not limited to, printed matter, videotape, computer readable disk, or optical disc.

Kits may also be provided that contain sufficient dosages of the compounds or composition to provide effective treatment for an individual for an extended period, such as a week, 2 weeks, 3, weeks, 4 weeks, 6 weeks, or 8 weeks or more.

The following examples are intended to illustrate, and not limit, the disclosed herein. For example, while the examples are noted to be for the isolation, purification and use of exosome compositions for the treatment of a fibrotic or liver disease or an associated disorder, the methods and compositions can be modified for the treatment of other fibrotic diseases as noted herein.

EXAMPLES

Example 1. Isolation of Exosomes for MiR Profiling

PureExo Exosome Isolation Kits were used to isolate serum exosomes. MiR profiling was performed on exosomal RNA from 1 ml of pooled serum (5 mice; 200 µl/mouse) using a mouse miRnome miR PCR Array. miR profiling was performed for the 940 best characterized miRs in the mouse miRnome on exosomes isolated from the circulation of mice after 1 or 5 weeks of treatment with $CCl_4$, as compared to oil-treated controls, with liver injury/fibrosis confirmed histologically. Balb/c mice were treated i.p. with corn oil (30 µl) or carbon tetrachloride (CCl$_4$; 4 µl CCl$_4$ diluted in 26 µl corn oil)) for up to 5 weeks. Differentially expressed miRs were confirmed and/or further evaluated by qRT-PCR of exosomal RNA independently obtained at 1-, 4- or 5-weeks of CCl$_4$ administration (n=5).

Isolated exosomes from mice serum were bi-membrane vesicles, 50-200 nm in diameter, and positive for the exosome markers, CD9 and flotillin-1. Microarray analysis revealed significant alterations in the expression of many hundreds of miRs after either 1- or 5-wks of CCl$_4$ treatment as compared to their respective oil controls. Applicants then focused on selected miRs previously reported to be altered in fibrotic liver, and confirmed the data by RT-PCR. The exosomal levels of these miRs after 5 weeks of CCl$_4$ (including up-regulation of miR-7a, -21, -22, -24, -34a, -155, -195, -455, -23b, -106a, -200b, -532, -34c, -151, -653, -687, and/or -483, and down-regulation of miR-27a, -192, -214, -377, -1906, -677, -541, -125b, -500, -466j, -544, -1a-2, -1194, and/or -700) reflected their previously documented changes at the tissue level in fibrotic liver. In addition, several exosomal miRs that have not yet to be reported in the literature as being altered during liver fibrosis emerged as potentially novel fibrosis markers (e.g. up-regulation of miR-26b or -122; down-regulation of miR-9 or -196b). As compared to their levels at 5 weeks, many of these miRs exhibited individually distinct patterns of expression during the course of fibrosis progression.

Dynamic changes occur in the miR content of circulating exosomes during experimental hepatic fibrosis supporting the concept that fibrosis progression and severity is amenable to minimally-invasive assessment through determination of signature exosomal miRs.

Example 2. MircoRNA (miR) Profiles of Circulating Exosomes from Healthy Mice are Distinct from Those of Mice with Hepatic Fibrosis MiR profiling was performed for the 940 best characterized miRs in the mouse miRnome on exosomes isolated from the circulation of mice after 1 or 5 weeks of treatment with CCl$_4$, as compared to oil-treated controls, with liver injury/fibrosis confirmed histologically; mice were treated i.p. with corn oil (30 µl) or carbon tetrachloride (CCl$_4$; 4 µl CCl$_4$ diluted in 26 µl corn oil) for 1 week or 5 weeks. (FIG. 1A). Of the several hundred miRs that were significantly up- or down-regulated in circulating exosomes as a function of CCl$_4$ versus oil and/or duration of CCl$_4$ exposure (FIG. 1A), Applicants then focused on selected miRs previously reported to be altered in fibrotic liver, and confirmed the data by RT-PCR. Chen, L., Charrier, A., Zhou, Y., Yu, B., Agarwal, K., Tsukamoto, H., Lee, L. J., Paulaitis, M. E., Brigstock, D. R. (2014) Epigenetic regulation of connective tissue growth factor by delivery of microRNA-214 in exosomes from mouse or human hepatic stellate cells *Hepatology* DOI:10.1002/hep.26768. PMID: 24122827.

As shown in FIG. 1B, the exosomal levels of these miRs often reflected their previously documented changes at the tissue level (including Applicants' own miR-214 data; Chen et al. (2014), supra). In addition, several exosomal miRs were validated by RT-PCR as potentially novel fibrosis markers even though they have not yet been reported to be altered in fibrotic livers. Many of these miRs exhibited individually distinct patterns of expression over time, highlighting that appropriately selected "slates" of exosomal miRs have biomarker potential for discriminating different stages of liver injury and/or fibrosis. This aside, the data show that the miR payload in circulating exosomes is altered during fibrosing liver injury.

Without being bound by theory, these data show that the molecular cargo in exosomes from healthy individuals reflects a non-disease status is that actually of potential therapeutic benefit when delivered in a setting of liver fibrosis.

Figure 2:
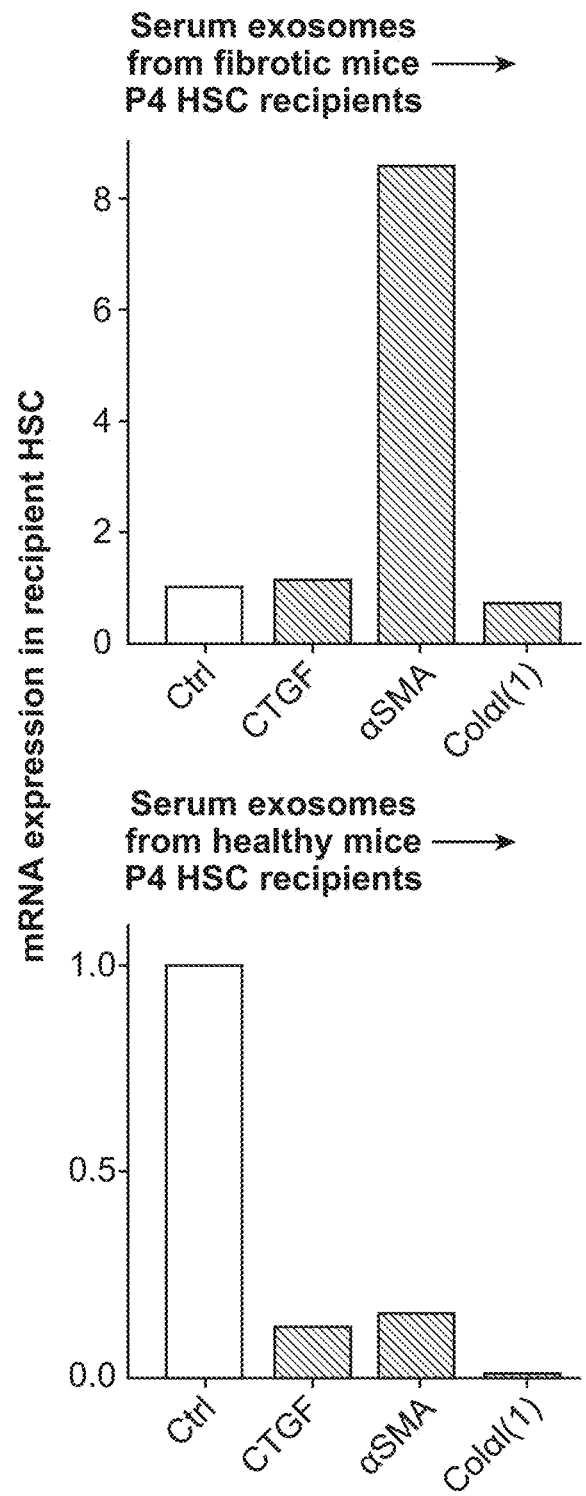
FIG. 2 shows fibrogenic gene expression in cultured hepatic stellate cell (HSC). Connective Tissue Growth Factor (CTGF), alpha smooth muscle actin (αSMA) or collagen α1(I) expression were assessed after 48-hr treatment of Day 9 primary HSC with exosomes purified from serum of mice with carbon tetrachloride-($CCl_4$)-induced liver fibrosis (upper) or that were healthy (lower). Exosomes from fibrotic mice either did not alter (CTGF, collagen) or exacerbated (αSMA) gene expression (upper) whereas exosomes from normal mice reduced expression of the same genes (lower).

Example 3. Exosomes from Serum of Normal Mice Reduce Expression of Pro-Fibrogenic Signals in In Vitro-Activated Hepatic Stellate Cells, the Principal Fibrosis-Producing Cells of the Liver Based on the significant differences between the payloads of exosomes from serum of normal versus fibrotic mice (FIGS. 1A & 1B), Applicants next tested whether these exosomes differentially regulated function of hepatic stellate cells (HSC). Although HSC are an usually quiescent cell type in the liver, during injury they become 'activated' and produce molecules that are pro-fibrogenic including connective tissue growth factor (CTGF), alpha smooth muscle actin (αSMA; a contractile protein that facilitates wound contraction/closure), and collagen (which is deposited as insoluble scar material). While HSC can be activated in vivo by many injurious agents, simply isolating the cells from normal non-injured liver and growing them in vitro causes them to undergo autonomous activation because they perceive the in vitro culture conditions as a wound environment. This process of culture-induced activation was used in this experiment. Culture-induced expression of CTGF, αSMA or collagen α1(I) in HSC on Day 9 of culture was reduced >90% following 48-hr incubation of the cells with exosomes isolated from the circulation of healthy mice (FIG. 2, lower) whereas circulating exosomes from fibrotic mice caused an 8-fold increase in αSMA expression and essentially no change in expression of CTGF or collagen α1(I) (FIG. 2, upper). Thus exosomes from the circulation of healthy, but not of fibrotic mice, significantly attenuated activation/fibrosis-related gene expression in HSC.

Figure 3A:
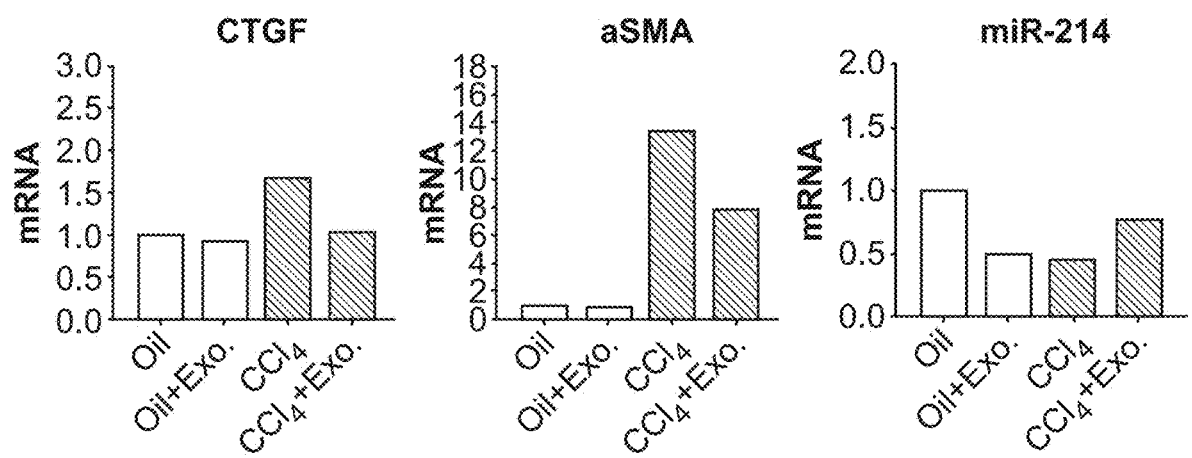
FIGS. 3A-3B show effect on CTGF, αSMA or miR-214 expression by activated HSC in vivo after concurrent treatment with CCl4 and serum exosomes. Mice received $CCl_4$ or oil (i.m) over a 7 day period, followed a few hours later by administration of exosomes (300 μl) i.p. On Day 9, HSC were harvested from each liver and briefly placed in culture for 24 hrs. The isolated HSC were then analyzed by (A) RT-PCR for mRNA expression or (B) immuno-cytochemistry (ICC) for protein production of key fibrogenic markers. $CCl_4$-induced expression of CTGF or αSMA was reduced by exosomes (A, B). Expression of miR-214, which is decreased during fibrosis, was increased to control levels by exosomes (A).
Figure 3B:
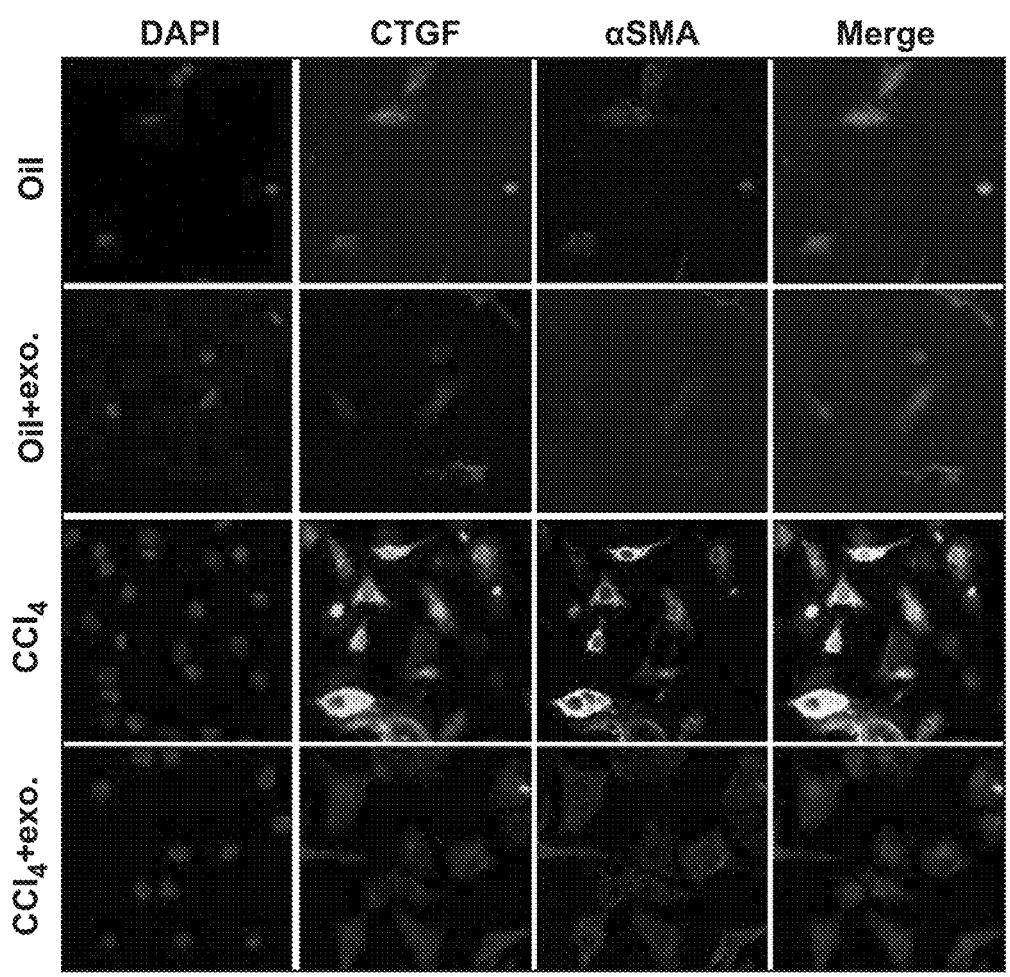

Example 4. Exosomes from Serum of Normal Mice Reduce Short-Term Expression of Pro-Fibrogenic Signals in Hepatic Stellate Cells In Vitro Following Activation of the Cells In Vivo with a Fibrotic Stimulus Applicants then tested whether serum exosomes could reverse fibrogenic gene expression in HSC after they had been activated in vivo. Mice received intramuscular injections (i.m.) of CCl$_4$ (in oil) or oil (carrier control) every other day for 1 week. On the same day, mice also received intraperitoneal (i.p.) injection of exosomes that had been purified from the serum of normal mice. On day 10, HSC were isolated, placed in culture for 1 day, and then analyzed. CCl$_4$-induced fibrogenic gene expression (FIG. 3A) and protein production (FIG. 3B) in HSC was attenuated by serum exosomes.

Example 5. Effect of Exosomes on CCl4-Induced Fibrotic Signaling in Mouse Livers Transgenic CTGF-EGFP mice that express enhanced green fluorescent protein (EGFP) under the control of the CTGF promoter were used in this experiment. In response to CCl$_4$ administration, these mice show liver-specific GFP induction. This response is principally attributed to CTGF induction in HSC during injury but other cells such as hepatocytes or Kupffer cells may contribute to the GFP-positive staining since CTGF may be upregulated in these cells during liver injury. Thus, examination of liver GFP fluorescence allowed Applicants to globally assess total CTGF production by all cell types in the liver. The CTGF-EGFP TG mouse is an extremely powerful and unique model in view of the very large dynamic changes that occur in GFP expression in a liver-specific manner, which is reflective of a massive induction in hepatic CTGF expression against a background CTGF expression which is normally very low in healthy mature mice.

Male or female mice received i.m. injections of $CCl_4$ (4 µl $CCl_4$ diluted in 26 µl corn oil) every other day for 1 week. On the same day, mice also received i.p injection of exosomes (100-300 µl; 3 µg/ul) that had been purified from the serum of normal mice. On day 10, livers were resected and examined.

Mice receiving exosome therapy had an overall more healthy appearance (better coat quality, etc., not shown) and livers from $CCl_4$-treated mice had surface nodules and were pale in appearance whereas those receiving exosomes were vascularized and smooth (=normal) (FIG. 4A). $CCl_4$ treatment caused a robust induction of GFP production which was dose-dependently inhibited by exosomes (FIGS. 4B & 4C). RT-PCR of total hepatic RNA showed that $CCl_4$-induced increases in CTGF and αSMA expression were reduced to baseline levels by exosomes (FIG. 4D).

Immunostaining for αSMA (marker of activated HSC) showed a substantial reduction in $CCl_4$-treated animals receiving exosomes as compared to those receiving CCl4 alone (FIG. 4E).

Example 6. Effect of Exosomes on CCl4-Induced Fibrosis in Mice

The purpose of this experiment is to expose mice to 5 weeks of $CCl_4$ to allow fibrosis to develop.

Male TG CTGF-EGFP mice were administered i.m. injection of $CCl_4$ (4 µl $CCl_4$ diluted in 26 µl corn oil) three times a week for 5 weeks. Starting at the beginning of week 4, some mice also received exosomes (from the circulation of healthy mice) by i.p. injection several hours after each $CCl_4$ injection during weeks 4 and 5 (100-300 µl; 3 ug/ul).

Induction of hepatic GFP (a surrogate of CTGF promoter activity) by GFP was attenuated by exosomes (FIG. 5A). RT-PCR showed that $CCl_4$-induced increase in CTGF, collagen, or αSMA expression and decreased in miR-214 expression trended to baseline in mice treated with exosomes (FIG. 5B). Immunostaining for αSMA, CTGF and collagen was strongly increased in $CCl_4$-treated animals but this was significantly reduced in mice on exosome therapy. (FIGS. 5C & 5D).

Example 7. MircoRNA (miR) Profiles of Circulating Exosomes from Healthy Mice are Distinct from Those of Mice with Hepatic Fibrosis Regardless of Selection Bias The data presented in Example 1 and FIGS. 1A & 1B compares progressive exosomal expression of selected miRs over time during fibrosis; however, this selection was inherently "biased" in the sense that the data was searched for miRs that had been previously implicated in fibrosis, or which were novel. Thus, the data was also analyzed in an unbiased method.

Figure 6:
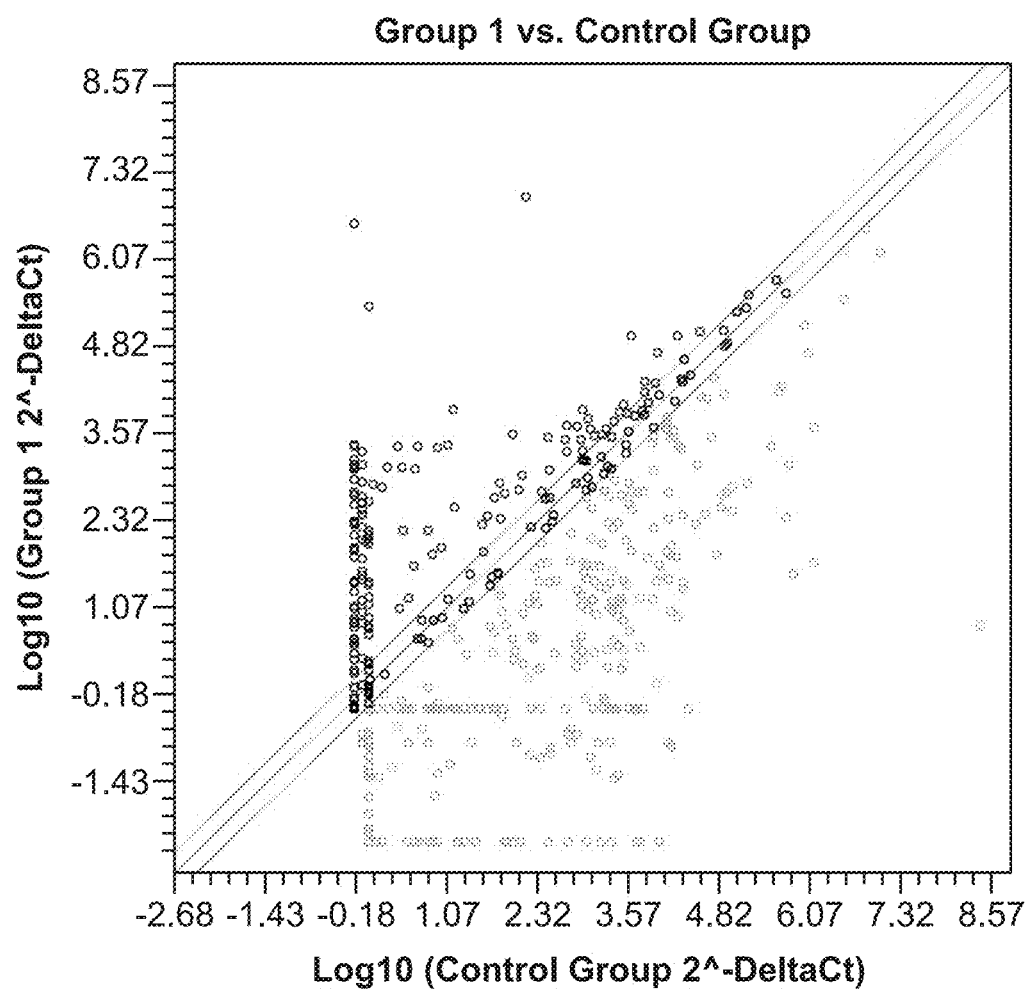
FIG. 6 shows differential expression of miRs in healthy and fibrotic mice. Exosomes from 1 ml of pooled serum (5 mice; 200 μl/mouse) were analyzed by miRnome miR PCR Array. The array compares exosomal miR expression in healthy mice relative to fibrotic mice to identify the principal components in serum that are expressed at relatively higher (Healthy$_{HIGH}$, darker shading) or lower (Healthy$_{LOW}$; lighter shading) levels in normal versus fibrotic mice. MiRs lying outside the diagonal line were expressed >±2-fold in healthy mice as compared to fibrotic mice. The "Top 10" Healthy$_{HIGH}$ and Healthy$_{LOW}$ miRs (highest differential expression).

Since exosomes from normal mice were shown to be are anti-fibrotic in mice with 5-week liver fibrosis, as shown above, the 5-week data shown in FIG. 1 was reanalyzed and ranked in an unbiased manner to identify the mIRs in the circulating exosomes that were most different between the groups. To facilitate this, the data were replotted using expression in normal animals as relative to that in fibrotic animals (this comparison to the prior examples). Data were ranked in a non-biased manner to identify exosomal miRs in serum from healthy mice that were expressed significantly higher ("$Healthy_{HIGH}$") or lower ("$Healthy_{LOW}$") than those in serum from fibrotic mice. (FIG. 6).

It was surmised that the anti-fibrotic activity of exosomes from healthy individuals was due, at least in part, to their high expression of $Healthy_{HIGH}$ miRs and low expression of $Healthy_{LOW}$ miRs.

Figures 7A, 7B, 7C, 7D, 7E, 7F, 7G, 7H, 7I:
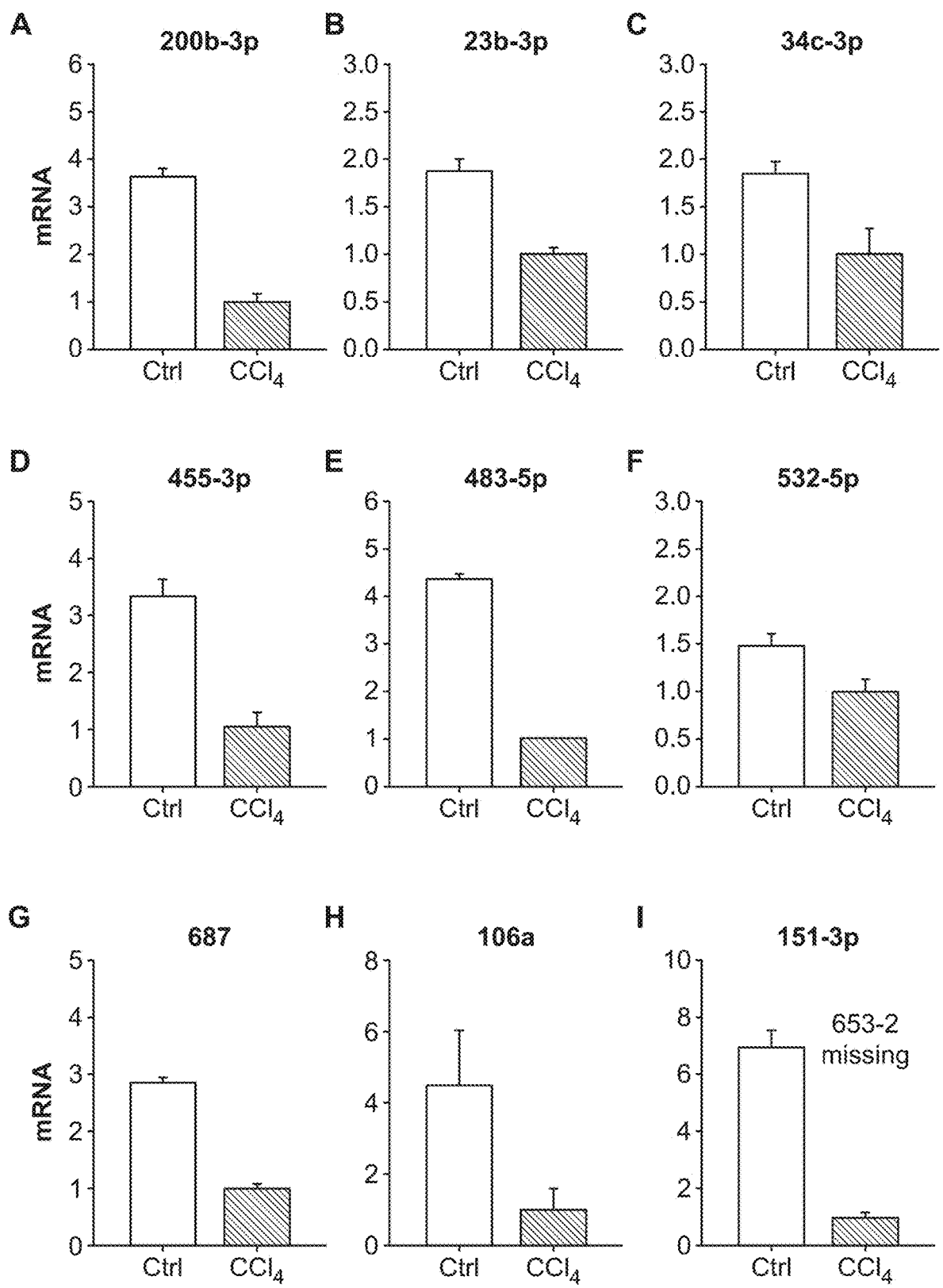
FIGS. 7A-7I show RT-PCR analysis of exosomal Healthy$_{HIGH}$ mIRs in circulating exosomes from control or fibrotic (CCL4-treated) mice. This experiment looked specifically at transcripts of (A) 200b-3p, (B) 23b-3p, (C) 34c-3p, (D) 455-3p, (E) 483-5p, (F) 532-5p, (G) 687, (H) 106a, and (I) 151-30

Next, RT-PCR was used to independently verify the differential array data by confirming reduced levels of $Healthy_{HIGH}$ miRs in fibrotic mice, as shown in FIG. 7. Analysis of miR 653-5p was also conducted, yielding similar results, but the data is not shown in FIG. 7.

Example 8. Effect of miRs on Fibrosis In Vitro

Figure 8A:
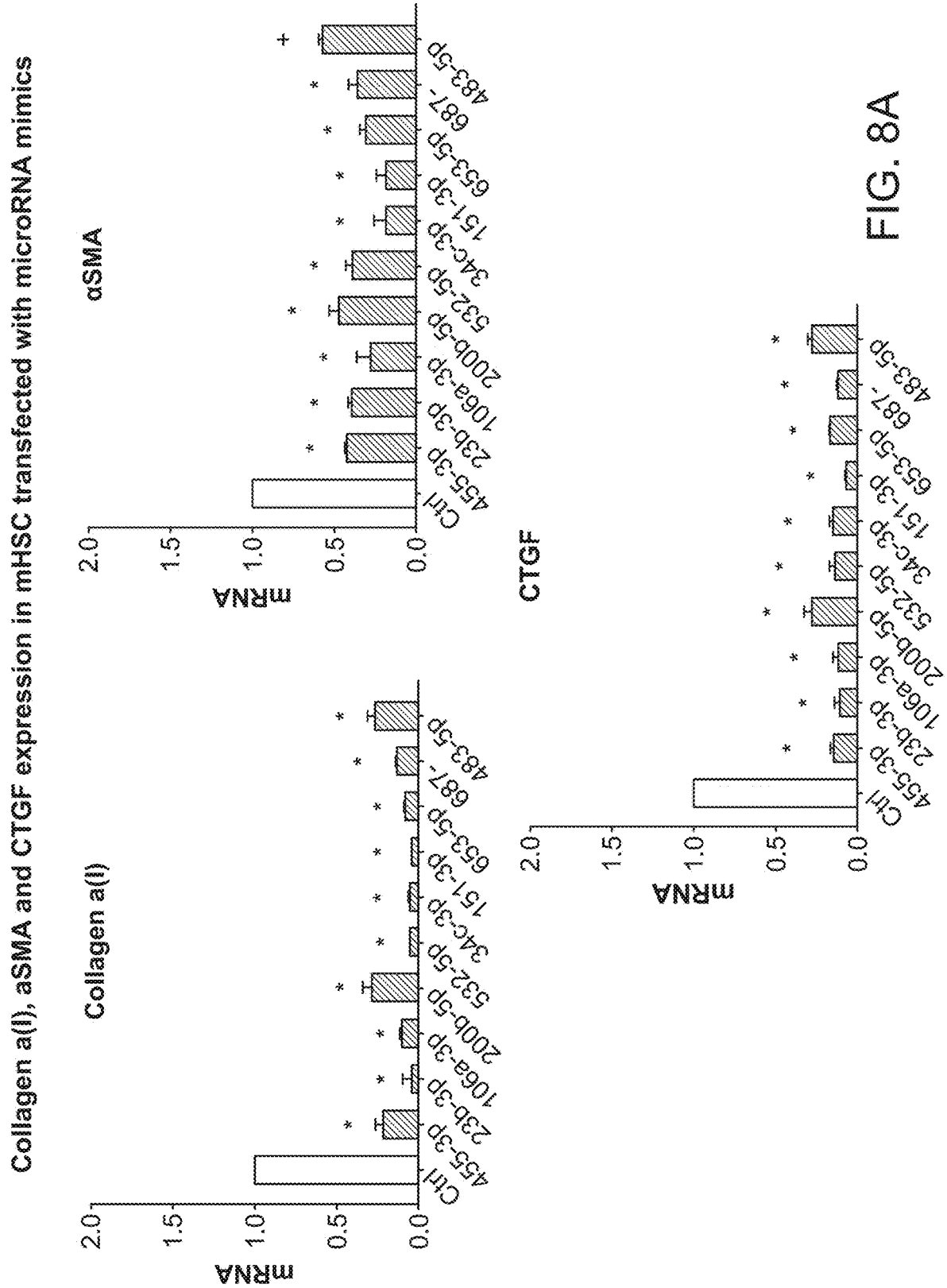
FIGS. 8A-8B show quantitative real-time polymerase chain reaction (qRT-PCR) for collagen α (I) or aSMA or CTGF mRNA relative to GAPDH mRNA in (FIG. 8A) mouse primary HSC or (FIG. 8B) human LX-2 HSC cells (B) transfected for 24 hrs with microRNA mimics (miR-455, -23b, -106a, -200b, -532, -34c, -151, -653, -687, or -483). A scramble microRNA mimic was used as a control (n=3 independent experiments performed in triplicate; *P<0.001 vs control, +P<0.01 vs control).
Figure 8B:
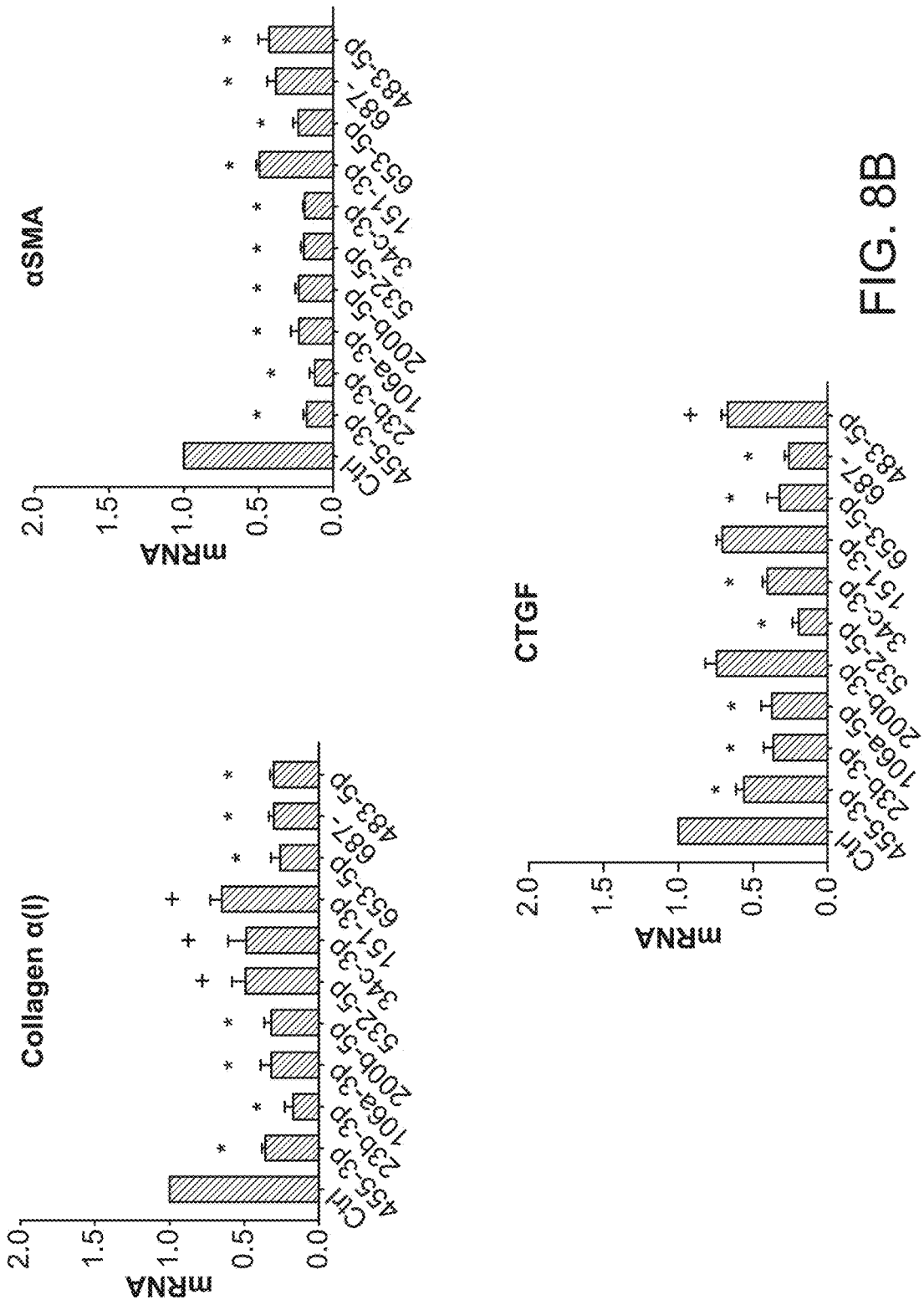

To determine whether the presence of $Healthy_{HIGH}$ miRs was causal of fibrosis, the ability for the miRs to individually attenuate the activated function in cultured mouse activated hepatic stellate cells, which are an in vitro test of fibrogenesis, was determined. This cell model was chosen because these cells drive the activated phenotype in fibrosing liver injury. Mimics of each mIR individually showed very significant anti-fibrotic activity by inhibiting expression of CTGF, αSMA, and/or collagen α(I), as shown in FIG. 8.

Rapid advances in the understanding of fibrogenesis and fibrosis have resulted in identification of a plethora of targets for anti-fibrotic therapy (Cohen-Naftaly, M. et al. (2011) Therap. Adv. Gastroenterol. 4(6):391-417; Ghiassi-Nejad, Z. et al. (2008) Expert Rev. Gastroenterol. Hepatol. 2(6): 803-816) but the most appropriate targets, type of therapeutic agent (e.g., cytotoxin, siRNA, miR, antibody, etc.), and mode of in vivo administration (carriers, delivery route, etc.) remains unclear. Since exosomes have evolved to protect their cargo from extracellular degradation and to deliver it into target cells, this function is exploitable as a novel therapeutic approach for liver fibrosis.

Applicants' disclosure is a novel application, namely to treat disease using exosomes that originate from the body fluids (urine saliva, lymphatic fluid, breast milk, blood, serum, and/or plasma) of healthy non-diseased subjects. Applicants' disclosure supports the concept of "banking" exosomes from healthy subjects for subsequent transfer back to the same subject when diseased, or alternatively to transfer to other diseased subjects. The disclosure has broad implications for treating a myriad of medical conditions extending far beyond those of the liver.

The methods as disclosed herein involve the transfer into subjects having fibrosis or fibrotic or hepatic disease or associated disorder of a composition comprising a naturally occurring organelle which, unlike other organelles, is released from the cells in which it is produced. These organelles are called "exosomes" and are tiny vesicles. During their production in their cells of origin, exosomes are packaged with a complex mixture of microRNA, mRNA, proteins and other molecules that are present in the producer cell and reflect its current biosynthetic and homeostatic state. Exosomes from cells in a healthy environment have a different molecular "payload" than those from an injury environment. Exosomes are released by the producer cell and shuttled to neighboring cells which take up the exosomal contents whereupon the recipient cell is reprogrammed according to the nature of the information received.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The disclosures illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for inhibiting the progression of or treating a fibrotic liver disease in a subject in need thereof, comprising administering to the subject a pharmaceutical composition comprising a pharmaceutically acceptable carrier and an effective amount of exosomes comprising a microRNA (miR)-26b level not higher than a miR-26b level and optionally a miR level of one or more miR-122, miR-9 or miR-196b of a subject that is not diagnosed as having the fibrotic liver disease that is to be inhibited or treated and wherein the exosomes are isolated from the serum of a subject not diagnosed with fibrotic liver disease.

2. The method of claim 1, wherein the fibrotic liver disease is caused by inflammation of the liver; high deposition of lipids, high deposition of insoluble collagen; or high deposition of extracellular matrix components; or wherein the subject has cirrhosis, hepatocarcinoma, or end-stage liver disease caused by the fibrotic liver disease.

3. The method of claim 1, further comprising determining the level of one or more of miR-26b, miR-122, miR-9, or miR-196b in a sample isolated from the subject prior or subsequent to the administration of the pharmaceutical composition.

4. The method of claim 1, further comprising determining the expression level of one or more, or two or more, or three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or twenty-eight or more, or twenty-nine or more, or thirty or more, or thirty-one or more, or thirty-two or more, or thirty-three or more, or thirty-four or more, or all of miR-7a, miR-21, miR-22, miR-24, miR-34a, miR-155, miR-195, miR-27a, miR-192, miR-214, miR-377, miR-455, miR-23b, miR-106a, miR-200b, miR-532, miR-34c, miR-26b, miR-122, miR-9, miR-196b, miR-151, miR-653, miR-687, miR-483, miR-1906, miR-677, miR-541, miR-125b, miR-500, miR-466j, miR-544, miR-1a-2, miR-1194, or miR-700, in a sample isolated from the subject prior or subsequent to the administration of the pharmaceutical composition.

5. The method of claim 1, wherein the subject is a mammal.

6. The method of claim 1, wherein the subject is a human.

7. The method of claim 1, wherein an effective amount comprises from 0.1 mg to about 1,000 mg per kg of body weight of the subject to be treated, in a single or multiple doses.

8. The method of claim 1, wherein the exosomes are allogeneic or autologous to the subject receiving the exosomes.

9. The method of claim 1, wherein the exosomes further comprise the miR-122 level of the subject that is not diagnosed as having the fibrotic liver disease.

10. The method of claim 9, wherein the exosomes further comprise the miR-9 level or the miR-196b level of the subject that is not diagnosed as having the fibrotic liver disease.

11. The method of claim 1, wherein the exosomes further comprise the miR-9 or miR-196b level of the subject that is not diagnosed as having the fibrotic liver disease.

12. The method of claim 1, wherein the exosomes further comprise the miR-9 level and the miR-196b level of the subject that is not diagnosed as having the fibrotic liver disease.

13. The method of claim 1, wherein the exosomes further comprise the miR-122 level, the miR-9 level and the miR-196b level of the subject that is not diagnosed as having the fibrotic liver disease.

14. The method of claim 1, wherein the exosomes further comprise a miR level of one or more, two or more, three or more, four or more, five or more, six or more, seven or more, eight or more, nine or more, ten or more, eleven or more, twelve or more, thirteen or more, fourteen or more, fifteen or more, or sixteen or more, or seventeen or more, or all of miR-7a, miR-122, miR-1906, miR-21, miR-22, miR-24, miR-34a, miR-155, miR-195, miR-677, miR-541, miR- 125b, miR-500, miR-466j, miR-544, miR-1a-2, miR-1194, or miR-700 of the subject that is not diagnosed as having the fibrotic liver disease.

15. The method of claim 1, wherein the exosomes further comprise a miR level of one or more, two or more, three or more, four or more, five or more, six or more, seven or more, eight or more, nine or more, ten or more, eleven or more, twelve or more, thirteen or more, fourteen or more, fifteen or more, or all of miR-27a, miR-192, miR-214, miR-377, miR-196b, miR-9, miR-455, miR-23b, miR-106a, miR-200b, miR-532, miR-34c, miR-151, miR-653, miR-687, or miR-483 of the subject that is not diagnosed as having the fibrotic liver disease.

16. The method of claim 1, wherein the exosomes further comprise a miR level of one or more, two or more, three or more, four or more, five or more, six or more, seven or more, eight or more, nine or more, ten or more, eleven or more, twelve or more, thirteen or more, fourteen or more, fifteen or more, or sixteen or more, or seventeen or more, or eighteen or more, nineteen or more, twenty or more, twenty one or more, twenty two or more, twenty three or more, twenty four or more, twenty five or more, twenty six or more, twenty seven or more, twenty eight or more, twenty nine or more, thirty or more, thirty one or more, thirty two or more, thirty three or more, or all of miR-7a, miR-122, miR-1906, miR-21, miR-22, miR-24, miR-34a, miR-155, miR-195, miR-677, miR-541, miR-125b, miR-500, miR-466j, miR-544, miR-1a-2, miR-1194, miR-700, miR-27a, miR-192, miR-214, miR-377, miR-196b, miR-9, miR-455, miR-23b, miR-106a, miR-200b, miR-532, miR-34c, miR-151, miR-653, miR-687, or miR-483 of the subject that is not diagnosed as having the fibrotic liver disease.

17. The method of claim 1, wherein the pharmaceutically acceptable carrier comprises one or more of saline, glycerol, or PBS.

18. The method of claim 17, wherein the pharmaceutically acceptable carrier further comprises a protease inhibitor.

19. The method of claim 1, wherein the pharmaceutical composition is formulated for low temperature storage below about 70° C., freeze-drying or lyophilisation.

* * * * *